(12) United States Patent
Chun et al.

(10) Patent No.: US 10,588,717 B2
(45) Date of Patent: Mar. 17, 2020

(54) DETACHABLE ORTHODONTIC BRACKET AND WIRE SYSTEM

(71) Applicant: Hankookin, Inc., Raleigh, NC (US)

(72) Inventors: James Jiwen Chun, Raleigh, NC (US); Andrew Youngho Chun, Raleigh, NC (US); Angela Soyoung Chun, Raleigh, NC (US); Jennifer Miseong Chun, Raleigh, NC (US)

(73) Assignee: Hankookin, Inc., Raleigh, NC (US)

( * ) Notice: Subject to any disclaimer, the term of this patent is extended or adjusted under 35 U.S.C. 154(b) by 107 days.

(21) Appl. No.: 15/297,174

(22) Filed: Oct. 19, 2016

(65) Prior Publication Data

US 2017/0105817 A1   Apr. 20, 2017

Related U.S. Application Data

(60) Provisional application No. 62/243,672, filed on Oct. 20, 2015.

(51) Int. Cl.
| | |
|---|---|
| A61C 7/10 | (2006.01) |
| A61C 7/06 | (2006.01) |
| A61C 7/08 | (2006.01) |
| A61C 7/20 | (2006.01) |
| A61C 7/12 | (2006.01) |
| A61C 7/28 | (2006.01) |

(Continued)

(52) U.S. Cl.
CPC ............ *A61C 7/10* (2013.01); *A61C 7/06* (2013.01); *A61C 7/08* (2013.01); *A61C 7/12* (2013.01); *A61C 7/145* (2013.01); *A61C 7/20* (2013.01); *A61C 7/28* (2013.01); *A61C 7/36* (2013.01)

(58) Field of Classification Search
CPC .... A61C 7/10; A61C 7/06; A61C 7/08; A61C 7/12; A61C 7/145; A61C 7/20; A61C 7/28; A61C 7/36; A61C 7/00
See application file for complete search history.

(56) References Cited

U.S. PATENT DOCUMENTS

| | | | | |
|---|---|---|---|---|
| 4,619,609 A | * | 10/1986 | Clark | A61C 7/36 433/6 |
| 5,415,542 A | * | 5/1995 | Kesling | A61C 7/08 433/6 |
| 7,234,935 B2 | | 6/2007 | Abels et al. | |

(Continued)

*Primary Examiner* — Heidi M Eide
*Assistant Examiner* — Drew S Folgmann
(74) *Attorney, Agent, or Firm* — Ashok Tankha

(57) ABSTRACT

A detachable orthodontic bracket and wire system includes bracket bases, brackets, and an arch wire for guiding alignment of teeth. The bracket bases are positioned on a lingual surface and/or a facial surface of the teeth. Each bracket base includes a first surface, a second surface, and at least one first interlocking element. The first surface is rigidly attached to the lingual surface and/or the facial surface of the teeth. The second surface opposes the lingual surface and/or the facial surface of the teeth. The first interlocking element is attached to and positioned in a direction substantially perpendicular to or parallel to the second surface of each bracket base. The brackets include at least second interlocking element that interlocks with the first interlocking element. The arch wire is inserted through a slot channel of each bracket. The bracket and the arch wire are infused and rigidly anchored within enclosing layers.

6 Claims, 31 Drawing Sheets

(51) Int. Cl.
*A61C 7/36* (2006.01)
*A61C 7/14* (2006.01)

(56) References Cited

U.S. PATENT DOCUMENTS

| | | |
|---|---|---|
| 7,234,936 B2 | 6/2007 | Lai et al. |
| 8,192,196 B2 | 6/2012 | Singh |
| 8,220,195 B2 | 7/2012 | Maijer et al. |
| 8,272,866 B2 | 9/2012 | Chun et al. |
| 8,979,528 B2 | 3/2015 | Macchi et al. |
| 9,192,453 B2 | 11/2015 | Rahimi |
| 2004/0115587 A1* | 6/2004 | Breining ............ A61C 7/00 433/24 |
| 2005/0186526 A1* | 8/2005 | Stewart ............ A61C 7/00 433/24 |
| 2005/0277084 A1* | 12/2005 | Cinader ............ A61C 7/20 433/20 |
| 2007/0184398 A1* | 8/2007 | Cronauer ............ A61C 7/00 433/6 |
| 2009/0061379 A1* | 3/2009 | Yamamoto ............ A61C 7/00 433/24 |
| 2011/0129786 A1* | 6/2011 | Chun ............ A61C 7/08 433/19 |
| 2013/0209952 A1* | 8/2013 | Kuo ............ A61C 7/002 433/10 |
| 2013/0230819 A1* | 9/2013 | Arruda ............ A61C 7/22 433/6 |
| 2014/0255865 A1* | 9/2014 | Gautam ............ A61C 7/28 433/9 |
| 2014/0302448 A1* | 10/2014 | Cassalia ............ A61C 7/28 433/9 |
| 2015/0216641 A1* | 8/2015 | Popa-Simil ............ A61C 19/04 433/8 |
| 2015/0335398 A1* | 11/2015 | Rosenthall ............ A61C 7/08 433/6 |
| 2015/0359610 A1* | 12/2015 | Carrillo Gonzalez ............ A61C 7/146 433/3 |

\* cited by examiner

DETACHABLE ORTHODONTIC BRACKET AND WIRE SYSTEM

CROSS-REFERENCE TO RELATED APPLICATIONS

This application claims priority to and the benefit of the provisional patent application No. 62/243,672 titled "Detachable Orthodontic Bracket And Wire System", filed in the United States Patent and Trademark Office on Oct. 20, 2015. The specification of the above referenced patent application is incorporated herein by reference in its entirety.

BACKGROUND

Orthodontic treatment involves repositioning of misaligned teeth to provide an improved appearance, bite relation, and masticating function. Repositioning teeth is accomplished by applying precision-controlled external forces to the teeth over a period of time. Orthodontists typically use one of two types of dental appliances to exert forces on the teeth, namely, fixed appliances and removable appliances.

Removable orthodontic appliances offer an alternative to conventional fixed orthodontic appliances. Minimal visibility during casual interactions is one of the benefits of removable orthodontic appliances. Patients generally prefer removable orthodontic appliances over fixed orthodontic appliances, because fixed orthodontic appliances are considered unsightly and are mostly used for adolescents. However, conventional removable orthodontic appliances lack strength, precision, and robustness of fixed orthodontic appliances which pose a problem for patients who require significant repositioning of teeth. Furthermore, removable orthodontic appliances may not always fit a patient's mouth properly, thereby causing pain or discomfort to the patient. This discomfort often negates the effectiveness of the orthodontic appliance.

To avoid a visible view of arch wires on a facial surface of the teeth, the arch wires are sometimes placed on the lingual surface of the teeth. Although some progress has been made with lingual placement of the arch wires, the small inter-bracket span, inaccessibility, and difficulty to adjust the arch wires make their use complicated. Thus, lingual placement is mostly used in simple and limited cases that involve minor tooth movement. Moreover, although a removable orthodontic appliance can use a wire and a bracket inside the removable orthodontic appliance to create a force for moving the teeth, the precision and strength of the removable orthodontic appliance are substantially less than the precision and the strength of fixed braces in which the bracket is bonded to the a surface of the teeth and in which the arch wires allow precise repositioning of the teeth. Therefore, there is a need for a system that is detachable and removable and can be precisely attached to a bonded base on a tooth for increasing the precision and the strength of the removable orthodontic appliance similar to a fixed bracket and wire system.

Hence, there is a long felt need for an orthodontic bracket and wire system that is detachably attachable to teeth with increased precision and strength for guiding alignment of teeth of an upper jaw or a lower jaw of a patient.

SUMMARY OF THE INVENTION

This summary is provided to introduce a selection of concepts in a simplified form that are further disclosed in the detailed description of the invention. This summary is not intended to determine the scope of the claimed subject matter.

The apparatus disclosed herein addresses the above recited needs for an orthodontic bracket and wire system detachably attachable to teeth with increased precision and strength for guiding alignment of teeth of an upper jaw or a lower jaw of a patient. The orthodontic bracket and wire system disclosed herein can be precisely attached to a bonded base on a tooth for increasing the precision and the strength of a removable orthodontic appliance.

The detachable orthodontic bracket and wire system disclosed herein comprises multiple bracket bases, multiple brackets, and at least one arch wire. The bracket bases are positioned on a lingual surface and/or a facial surface of a patient's teeth. Each of the bracket bases comprises a first surface, a second surface, and at least one first interlocking element. The first surface of each of the bracket bases is rigidly attached to the lingual surface, or the facial surface, or both the lingual surface and the facial surface of the teeth. The second surface of each of the bracket bases opposes the lingual surface and/or the facial surface of the teeth. The first interlocking element is attached to the second surface of each of the bracket bases and is positioned in a direction substantially perpendicular to or a direction substantially parallel to the second surface of each of the bracket bases.

Each of the brackets of the detachable orthodontic bracket and wire system comprises at least one second interlocking element configured to interlock with the corresponding first interlocking element of each of the bracket bases in the direction substantially perpendicular to or the direction substantially parallel to the second surface of each of the bracket bases. Each of the brackets further comprises a slot channel passing through each of the brackets. The arch wire is inserted through the slot channel of each of the brackets positioned on the lingual surface and/or the facial surface of the teeth. The arch wires extend from a molar region on a first side of a dental arch to a molar region on a second side of the dental arch. The arch wire is infused and rigidly anchored within an inner lingual side and/or an inner facial side of enclosing layers.

In an embodiment, the detachable orthodontic bracket and wire system further comprises a primary frame wire positioned on the facial surface and the lingual surface of the teeth and traverses from the facial surface to the lingual surface of the teeth through cusps of the teeth. The primary frame wire secures and anchors the brackets interlocked to the bracket bases to the teeth and provides strong orthodontic forces to the teeth. In another embodiment, the detachable orthodontic bracket and wire system further comprises one or more secondary frame wires anchored to the arch wire or the primary frame wire. The secondary wires are rigidly positioned individually around each of the teeth to allow each of the teeth to move independent of each other.

BRIEF DESCRIPTION OF THE DRAWINGS

The foregoing summary, as well as the following detailed description of the invention, is better understood when read in conjunction with the appended drawings. For the purpose of illustrating the invention, exemplary constructions of the invention are shown in the drawings. However, the invention is not limited to the specific methods and structures disclosed herein. The description of a method step or a structure referenced by a numeral in a drawing is applicable to the description of that method step or structure shown by that same numeral in any subsequent drawing herein.

DETAILED DESCRIPTION OF THE INVENTION

Figure 1:
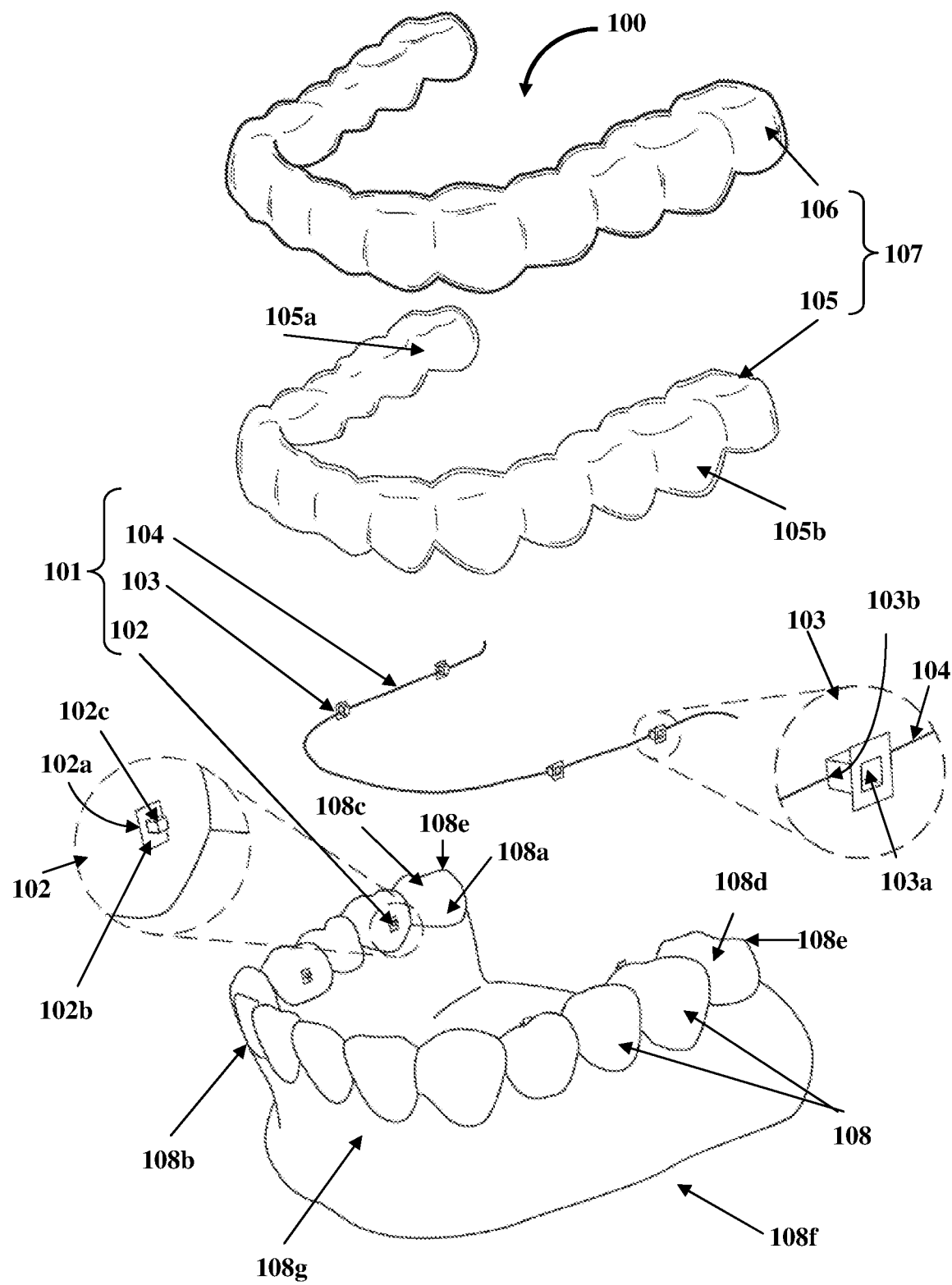
FIG. 1 exemplarily illustrates an exploded view of a removable orthodontic appliance, showing a detachable orthodontic bracket and wire system for guiding alignment of teeth of a lower jaw of a patient.

FIG. 1 exemplarily illustrates an exploded view of a removable orthodontic appliance 100, showing a detachable orthodontic bracket and wire system 101 for guiding the alignment of teeth 108 of a lower jaw 108f of a patient. The removable orthodontic appliance 100 is a trough shaped arch tray that defines a space between substantially vertical sides of the arch tray for accommodating the teeth 108 of an upper jaw (not shown) or a lower jaw 108f. As exemplarily illustrated in FIG. 1, the removable orthodontic appliance 100 is detachably attached to teeth 108 of the lower jaw 108f. In an embodiment (not shown), the removable orthodontic appliance 100 is detachably attachable to teeth 108 of the upper jaw (not shown). The detachable orthodontic bracket and wire system 101 disclosed herein is detachably attached to the teeth 108 and enclosed by enclosing layers 107 as exemplarily illustrated in FIG. 2. The enclosing layers 107 comprise a first soft enclosing layer 105 and a second hard enclosing layer 106. The soft enclosing layer 105 is, for example, made of a soft plastic, for example, polyethylene, polyester, ethylene vinyl acetate (EVA), etc. The second hard enclosing layer 106 is, for example, made of a hard plastic, for example, a polyethylene-vinyl acetate copolymer. The detachable orthodontic bracket and wire system 101 can be used on both inner lingual side 105a and inner facial side 105b of the enclosing layer 106. The detachable orthodontic bracket and wire system 101 guides alignment of the teeth 108 of an upper jaw or a lower jaw 108f of a patient.

The detachable orthodontic bracket and wire system 101 disclosed herein comprises multiple bracket bases 102, multiple brackets 103, and at least one arch wire 104. As exemplarily illustrated in FIG. 1, the bracket bases 102 are positioned on a lingual surface 108a of the patient's teeth 108. In an embodiment (not shown), the bracket bases 102 are positioned on a facial surface 108b of the patient's teeth 108. In another embodiment (not shown), the bracket bases 102 are positioned on both the lingual surface 108a and the facial surface 108b of the patient's teeth 108. The bracket bases 102 are bonded and cemented directly on the lingual surface 108a and/or the facial surface 108b of the teeth 108. The bracket bases 102 are made of, for example, a rigid metal, or an acrylic material, or a composite material, or a ceramic material, etc., or in an embodiment, any combination thereof. The shape of each bracket base 102 and the number and distribution of the bracket bases 102 in the detachable orthodontic bracket and wire system 101 is configurable and can be changed based on the requirement of the teeth 108 to be aligned, etc. The brackets 103 are interlocked with the bracket bases 102 as disclosed in the detailed description of FIGS. 4A-4D, FIGS. 5A-5B, and FIGS. 6A-6B.

The orthodontic bracket and wire system 101 disclosed herein is detachable and has a strong interlocking strength when attached to the teeth 108. The bracket bases 102 and the brackets 103 of the detachable orthodontic bracket and wire system 101 are manufactured with high precision and physical strength for delivering a precise and strong orthodontic force to attach the removable orthodontic appliance 100 firmly to the teeth 108. As used herein, "orthodontic force" refers to a mechanical force applied to the teeth 108 to optimally align the teeth 108 as required by an orthodontist. The detachable orthodontic bracket and wire system 101 is bonded to teeth 108 that are required to be actively and precisely moved in a predefined direction to ensure a predictable teeth configuration. Clear or white colored bracket bases 102 can be used in the detachable orthodontic bracket and wire system 101 for esthetic appearance. While the detachable orthodontic bracket and wire system 101 transfers the orthodontic force from the arch wire 104 to each tooth 108, the primary source of orthodontic forces is produced from the arch wire 104. Since the arch wire 104 is detachable and not fixed to the teeth 108, the detachable orthodontic bracket and wire system 101 provides a stable, enclosed, rigid and elastic framework that allows the original shape of the arch wire 104 to be retained when the arch wire 104 is attached and detached from the teeth 108.

As exemplarily illustrated in FIG. 1, the bracket base 102 is positioned on a lingual surface 108a of the teeth 108. The bracket base 102 is fixedly attached to the teeth 108 using adhesive materials, for example, bonding cement. In an embodiment (not shown), the bracket base 102 is positioned on a facial surface 108b of the teeth 108. Each bracket base 102 comprises a first surface 102a, a second surface 102b, and at least one first interlocking element 102c as exemplarily illustrated in FIGS. 4A-4D, FIGS. 5A-5B, FIGS. 6A-6B, FIGS. 8A-8B, FIGS. 9A-9B, FIGS. 10A-10B, and FIGS. 11A-11B. The first surface 102a of each bracket base 102 is rigidly attached to the lingual surface 108a of the teeth 108. In an embodiment (not shown), the first surface 102a of each bracket base 102 is rigidly attached to the facial surface 108b of the teeth 108. In another embodiment (not shown), first surfaces 102a of the bracket bases 102 are rigidly attached to the lingual surface 108a and the facial surface 108b of the teeth 108. The lingual surface 108a and/or the facial surface 108b of the teeth 108 are coated with an adhesive material, for example, bonding cement that affixes the first surface 102a of the bracket base 102 to the lingual surface 108a and/or the facial surface 108b of the teeth 108. In an embodiment, the bonding cement is coated on the first surface 102a of the bracket base 102 and used to attach the first surface 102a of the bracket base 102 to the lingual surface 108a and/or the facial surface 108b of the teeth 108. In another embodiment, the bonding cement is coated on both the lingual surface 108a and/or the facial surface 108b of the teeth 108 and the first surface 102a of the bracket base 102. The second surface 102b of each bracket base 102 opposes the lingual surface 108a and/or the facial surface 108b of the teeth 108. As exemplarily illustrated in FIG. 1, the first interlocking element 102c is attached to and extends from the second surface 102b of the bracket base 102. In an embodiment, the first interlocking element 102c is detachably attached to the second surface 102b of the bracket base 102. The first interlocking element 102c is positioned in a direction substantially perpendicular to the second surface 102b of each bracket base 102 as disclosed in the detailed description of FIGS. 12A-12B. In an embodiment, the first interlocking element 102c is positioned in a direction substantially parallel to the second surface 102b of each bracket base 102 as disclosed in the detailed description of FIGS. 13A-13B.

Figure 12A:
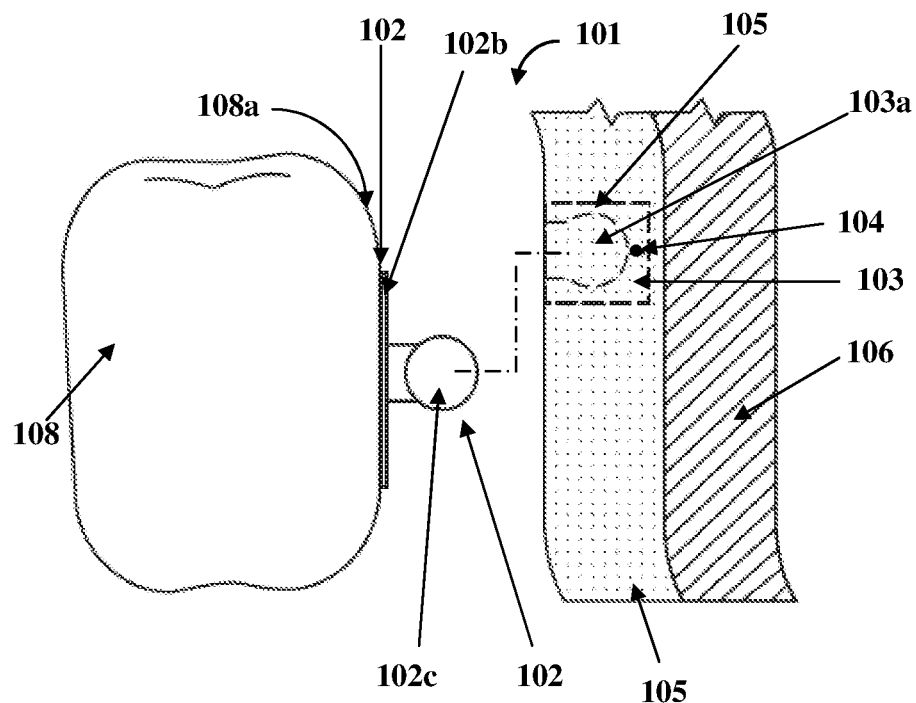
FIG. 12A exemplarily illustrates a disassembled partial sectional view of an embodiment of the detachable orthodontic bracket and wire system, showing positioning of a first interlocking element in a direction substantially perpendicular to a second surface of the bracket base.
Figure 12B:
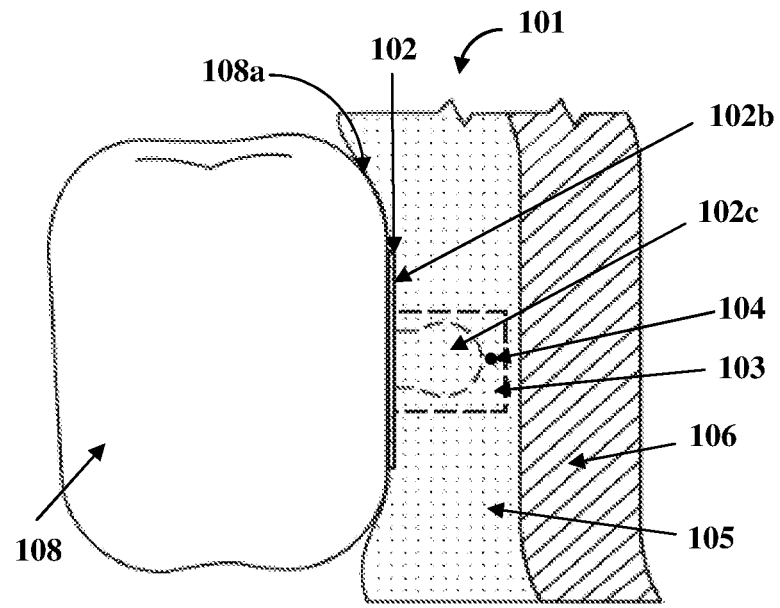
FIG. 12B exemplarily illustrates an assembled partial sectional view of the embodiment of the detachable orthodontic bracket and wire system, showing attachment of the bracket to the bracket base shown in FIG. 12A, in a direction substantially perpendicular to the second surface of the bracket base.
Figure 13A:
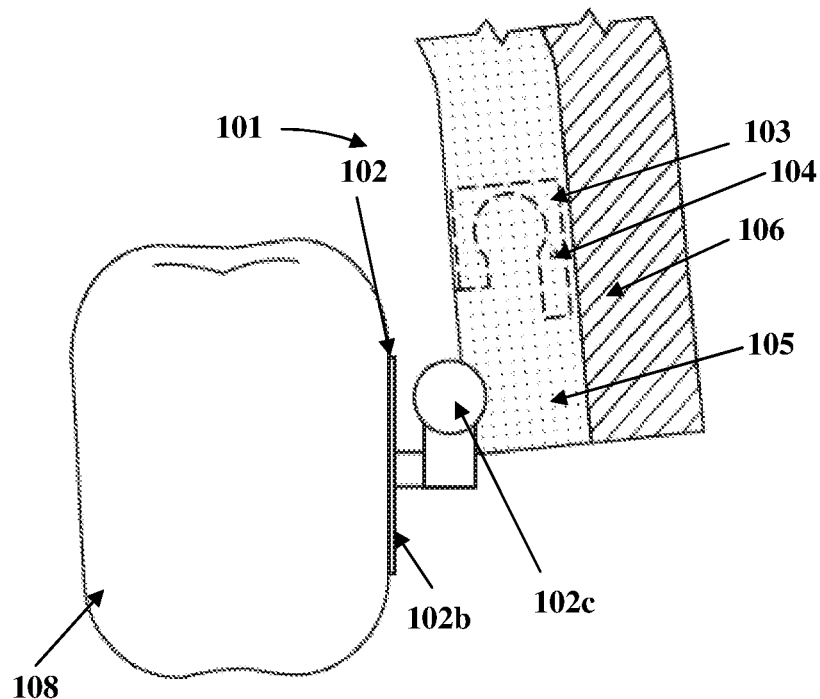
FIG. 13A exemplarily illustrates a disassembled partial sectional view of an embodiment of the detachable orthodontic bracket and wire system, showing the positioning of the first interlocking element in a direction substantially parallel to the second surface of the bracket base.
Figure 13B:
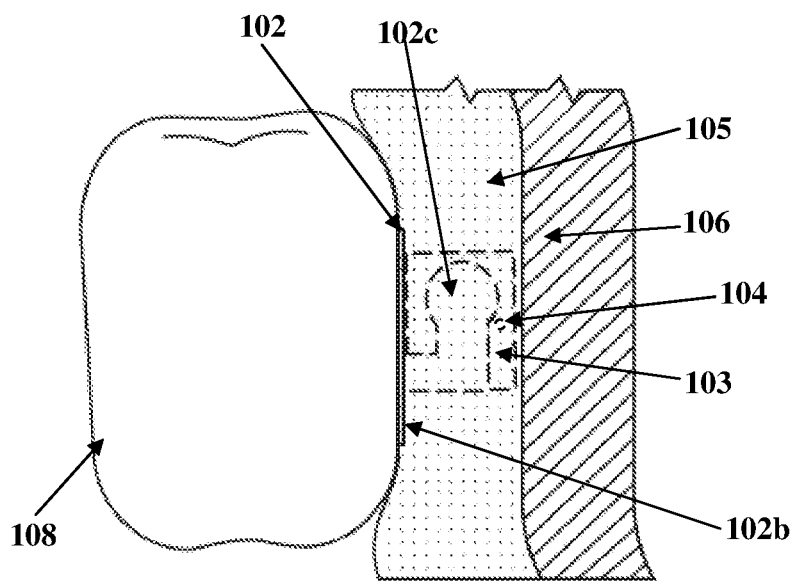
FIG. 13B exemplarily illustrates an assembled partial sectional view of the embodiment of the detachable orthodontic bracket and wire system, showing attachment of the bracket to the bracket base shown in FIG. 13A, in a direction substantially parallel to the second surface of the bracket base.

As exemplarily illustrated in FIG. 1, each bracket 103 of the detachable orthodontic bracket and wire system 101 comprises at least one second interlocking element 103a configured to interlock with a corresponding first interlocking element 102c of each bracket base 102 exemplarily illustrated in FIG. 1, in a direction substantially perpendicular to the second surface 102b of the bracket base 102 as disclosed in the detail description of FIGS. 12A-12B, and in an embodiment, in a direction substantially parallel to the second surface 102b of the bracket base 102 as disclosed in the detail description of FIGS. 13A-13B. The interlocking elements 102c and 103a can be of multiple different shapes. The first interlocking element 102c of each bracket base 102 is configured, for example, as an oval projection, a circular projection, a square projection, a cuboidal projection, a cylindrical projection, etc. Non-circular shaped projections and two or more projections provide better force control than a single projection. For example, a double base projection provides a better anchor for a bending force.

The second interlocking element 103a of each bracket 103 is configured as a receptacle of a corresponding shape to interlock the first interlocking element 102c of each bracket base 102. The bracket 103 further comprises a slot channel 103b passing through each bracket 103 as exemplarily illustrated in FIG. 4A and FIG. 4C. The slot channel 103b of the bracket 103 is positioned proximal to an inner lingual side 105a of the first soft enclosing layer 105 exemplarily illustrated in FIG. 1, or in an embodiment (not shown) to an inner facial side 105b of the first soft enclosing layer 105, or in another embodiment (not shown) to the inner lingual side 105a and the inner facial side 105b of the first soft enclosing layer 105.

As illustrated in FIG. 1, the arch wire 104 is inserted through the slot channel 103b of each bracket 103. The arch wire 104 extends from a molar region 108c on a first side of a dental arch 108g to a molar region 108d on a second side of the dental arch 108g. The slot channel 103b is configured with a predefined cross section, for example, a circular cross section to accommodate the arch wire 104 configured with the same predefined cross section, for example, the circular cross section. The function of the arch wire 104 is to align the teeth 108 along the path of the arch wire 104. The arch wire 104 and each bracket 103 are infused and rigidly anchored within the inner lingual side 105a and/or the inner facial side 105b of the first soft enclosing layer 105, for example, via heat infusion as disclosed in the detailed description of FIG. 2. The arch wire 104 and each bracket 103 are infused and rigidly anchored within the inner lingual side 105a of the first soft enclosing layer 105. In an embodiment (not shown), the arch wire 104 and each bracket 103 are infused and rigidly anchored within the inner facial side 105b of the first soft enclosing layer 105. In another embodiment (not shown), the arch wire 104 and each bracket 103 are infused and rigidly anchored within the inner lingual side 105a and the inner facial side 105b of the first soft enclosing layer 105. In another embodiment, the arch wire 104 and each bracket 103 are infused and rigidly anchored within the inner lingual side 105a and/or the inner facial side 105b of the first soft enclosing layer 105 and within an inner lingual side (not shown) and/or an inner facial side (not shown) of the second hard enclosing layer 106. The arch wire 104 that runs through the slot channel 103b of each bracket 103 provides an arch form and a force, for example, a translational force applied against the teeth 108 to be aligned. The slot channel 103b allows translational motion of the arch wire 104 through an open space in the slot channel 103b. When the slot channel 103b has a rectangular cross section and the arch wire 104 has a rectangular cross section as exemplarily illustrated in FIGS. 4C-4D, the slot channel 103b exerts a torque on the arch wire 104 through side walls of the slot channel 103b similar to a torque mechanism in a fixed bracket system.

Figure 2:
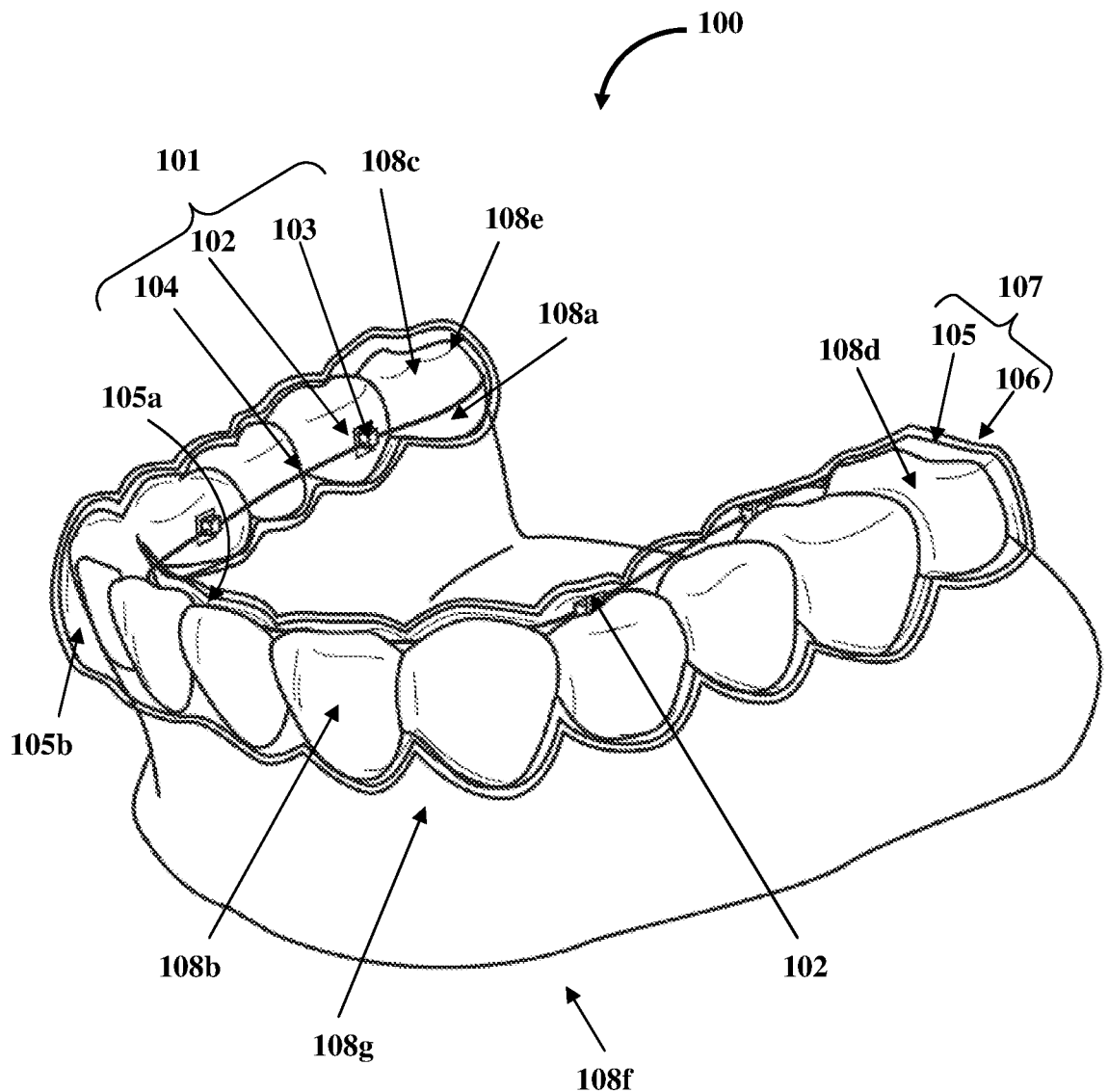
FIG. 2 exemplarily illustrates an assembled isometric view of the removable orthodontic appliance comprising the detachable orthodontic bracket and wire system positioned on teeth of a lower jaw.

FIG. 2 exemplarily illustrates an assembled isometric view of the removable orthodontic appliance 100 comprising the detachable orthodontic bracket and wire system 101 positioned on the teeth 108 of the lower jaw 108f. The detachable orthodontic bracket and wire system 101 are enclosed by the enclosing layers 107. The enclosing layers 107 comprise a first soft enclosing layer 105 and a second hard enclosing layer 106. The enclosing layers 107 are placed on the teeth 108 after the bracket bases 102 and the assembly of the brackets 103 and the arch wire 104 are positioned on the teeth 108. In areas of the teeth 108 and gum surface without the assembly of the brackets 103 and the arch wire 104, the first soft enclosing layer 105 is positioned directly over the teeth 108 or gum surface. The first soft enclosing layer 105 provides support and remains elastic to transmit orthodontic forces from the arch wire 104 to the teeth 108. The first soft enclosing layer is, for example, a soft layer made of a plastic material. In an embodiment, the first soft enclosing layer 105 is made from other soft materials, for example, polyethylene, polyester, ethylene vinyl acetate (EVA), etc. The first soft enclosing layer 105 infuses and rigidly anchors each bracket 103 and the arch wire 104 inserted through the slot channel 103b of each bracket 103. As exemplarily illustrated in FIG. 2, the first soft enclosing layer 105 infuses with each bracket 103 and the arch wire 104 at the inner lingual side 105a of the first soft enclosing layer 105. In an embodiment (not shown), the first soft enclosing layer 105 infuses with each bracket 103 and the arch wire 104 at the inner facial side 105b of the first soft enclosing layer 105. The first soft enclosing layer 105 encloses the teeth 108 on the lingual surface 108a and the facial surface 108b of the teeth 108 as exemplarily illustrated in FIG. 2. In an embodiment, the first soft enclosing layer 105 is first placed over the teeth 108 and a portion of the first soft enclosing layer 105 is cut out around the bracket base 102 to allow placement of the assembly of the brackets 103 and the arch wire 104 over the first soft enclosing layer 105.

The second hard enclosing layer 106 encloses the first soft enclosing layer 105. In an embodiment, a thin second hard enclosing layer 106 is sprayed or heat fused over the first soft enclosing layer 105 to provide extra rigidity to the removable orthodontic appliance 100. The second hard enclosing layer 106 is, for example, a thin hard layer made of a plastic material. In an embodiment, the second hard enclosing layer 106 is made of different hard materials, for example, a polyethylene-vinyl acetate copolymer. In an embodiment, the second hard enclosing layer 106 infuses and rigidly anchors each bracket 103 and the arch wire 104. The second hard enclosing layer 106 encloses the first soft enclosing layer 105 and in turn, the lingual surface 108a of the teeth 108 and the facial surface 108b of the teeth 108.

The detachable orthodontic bracket and wire system 101 is embedded in the enclosing layers 107 via heat infusion. The arch wire 104 is configured to maximize the liquid flow of viscous melted plastic to each void between the teeth 108 and the arch wire 104. In an embodiment, for increasing the strength of the infusion, a coating of a hard plastic material or an adhesive is coated on the arch wire 104 and the brackets 103, and as the coating of the hard plastic material melts, the hard plastic material infuses with the first soft enclosing layer 105 made, for example, of a soft plastic material. In an example, the arch wire 104 is coated with a thin layer of hard plastics. The hard plastics, when heated, bond better with the first soft enclosing layer 105. In an embodiment, the heating process is accomplished by placing a positive electrode and a negative electrode at the two ends of the arch wire 104 and using an electric current to heat the metal material of the arch wire 104 to a predetermined temperature which melts the plastic material of the enclosing layers 107 to fuse with the arch wire 104 and the brackets 103. In another embodiment, the arch wire 104 is heated by microwave heating which provides heat only to the metal material of the arch wire 104.

The second hard enclosing layer 106 is placed over the first soft enclosing layer 105 to provide better rigidity and resilience. The second hard enclosing layer 106 is rigid for protection and the first soft enclosing layer 105 is flexible for ease and comfort of fitting onto the teeth 108. Softer plastics, for example, polyethylene can be used for making the enclosing layers 107 when more elastic force is needed to pull the teeth 108 together. Materials such as Zendura® of Bay Materials LLC that offer both rigidity and resilience can be used to make the enclosing layers 107, when moderate level forces are needed to pull the teeth 108 together. The thickness of the plastic material of each of the enclosing layers 107 is, for example, from about 0.5 mm to about 2 mm, so that the plastic material offers elasticity to fit the removable orthodontic appliance 100 onto the teeth 108, while the arch wire 104 retains its elasticity. The enclosing layers 107 provide an elastic framework to the detachable orthodontic bracket and the wire system 101 and retain the shape of the arch wire 104 inserted in the slot channel 103b of each bracket 103 exemplarily illustrated in FIG. 1. The enclosing layers 107 facilitates easy removal of the detachable orthodontic bracket and wire system 101 since the enclosing layers 107 are infused in the arch wire 104. The enclosing layers 107 protect the teeth 108 from impact and prevent collection of food particles in the detachable orthodontic bracket and wire system 101. The detachable orthodontic bracket and wire system 101 comprising the bracket bases 102, the brackets 103, the arch wire 104, and the enclosing layers 107 constitute the arch tray, herein referred to as the "removable orthodontic appliance".

Figure 3A:
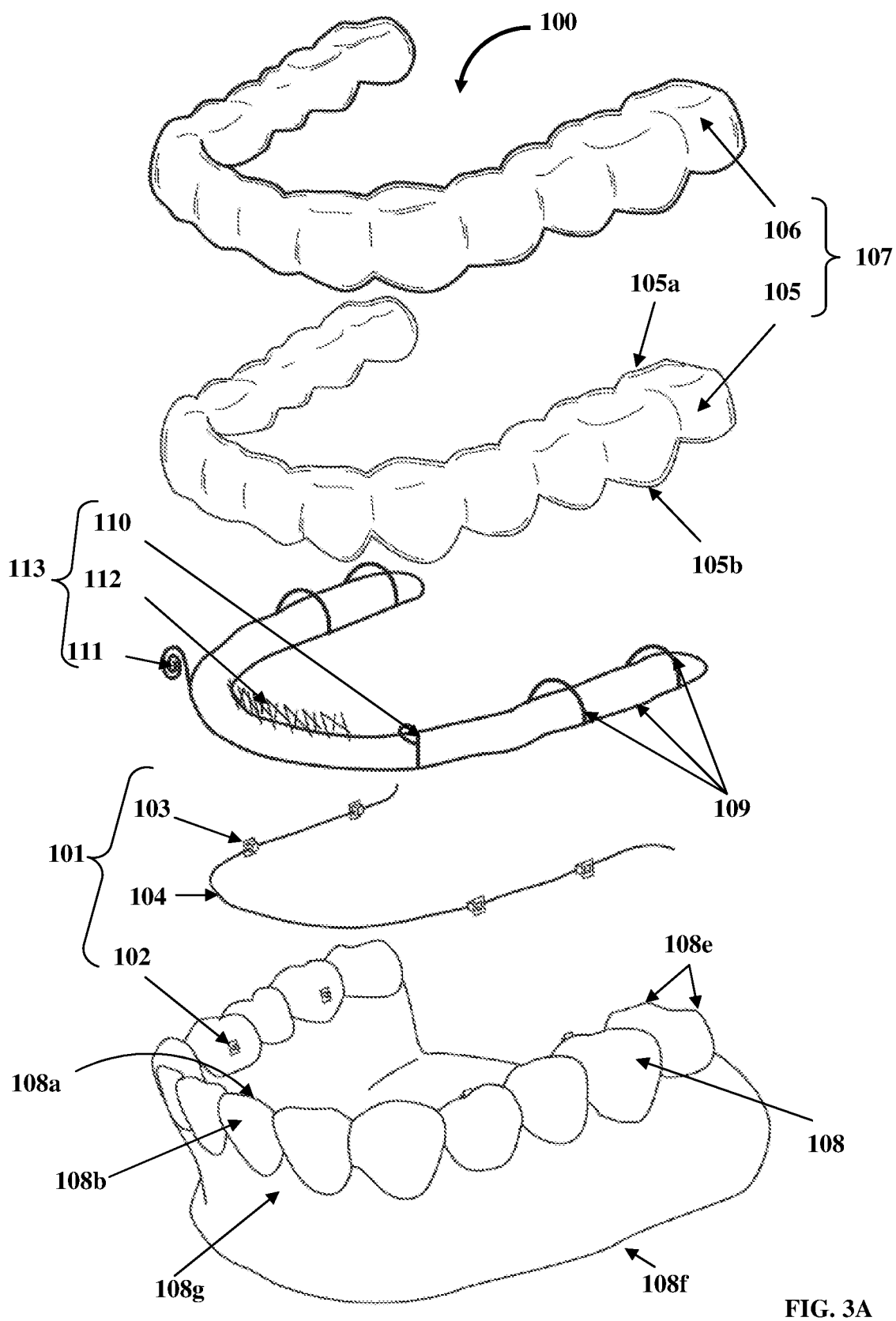
FIG. 3A exemplarily illustrates an exploded view of the removable orthodontic appliance, showing an embodiment of the detachable orthodontic bracket and wire system comprising a primary frame wire and secondary frame wires.

FIG. 3A exemplarily illustrates an exploded view of the removable orthodontic appliance 100, showing an embodiment of the detachable orthodontic bracket and wire system 101 comprising a primary frame wire 109 and secondary frame wires 113. In an embodiment, in addition to the bracket bases 102, the brackets 103, and the arch wire 104 disclosed in the detailed description of FIG. 1, the detachable orthodontic bracket and wire system 101 further comprises a primary frame wire 109 and one or more secondary frame wires 113. In this embodiment, there are different types of wires in the detachable orthodontic bracket and wire system 101, for example, the arch wire 104 that produces the orthodontic force, and the primary frame wire 109 and/or the secondary frame wires 113 that support the arch wire 104 into a rigid and elastic framework. The primary frame wire 109 is positioned on the facial surface 108b and the lingual surface 108a of the teeth 108. The primary frame wire 109 traverses from the facial surface 108b to the lingual surface 108a of the teeth 108 through cusps 108e of the teeth 108. The primary frame wire 109 secures and anchors the brackets 103 interlocked to the bracket bases 102 to the teeth 108 and provides strong orthodontic forces to the teeth 108 for aligning the teeth 108. The primary frame wire 109 maintains the elasticity of the entire removable orthodontic appliance 100. The primary frame wire 109 is made of a metal wire or a fiberglass wire that retains elasticity for a longer time than a plastic material used for conventional, clear and removable orthodontic appliances. The primary frame wire 109 is coated with a color that matches teeth 108 or gums, for example, white, pink, etc. The primary frame wires 109 coated, for example, with a white color can run between the cusps 108e of the teeth 108 and embrace the main anchoring teeth such as canines and molars. The primary frame wire 109 secures and anchors the brackets 103 and runs from the lingual surface 108a of the teeth 108 to the facial surface 108b of the teeth 108. The primary frame wire 109 can be positioned between any of the teeth 108 or all of the teeth 108 from the facial surface 108b to the lingual surface 108a of the upper jaw (not shown) and the lower jaw 108f of the teeth 108 along gum lines. In an embodiment, additional primary frame wires 109 are incorporated in the detachable orthodontic bracket and wire system 101 as needed for guiding alignment of the teeth 108 of the upper jaw and the lower jaw 108f. In an embodiment, the arch wire 104 is either soldered together with the primary frame wire 109 or is detached from the primary frame wire 109.

In an embodiment, the orthodontic bracket and wire system 101 further comprises one or more secondary frame wires 113, also referred to as "mini-frame wires", rigidly positioned individually around each of the teeth 108 to allow each of the teeth 108 to move independent of each other. The secondary frame wire 113 facilitates independent movement of the teeth 108 by anchoring to the primary frame wire 109. In an embodiment, the secondary frame wire 113 is anchored to the arch wire 104 as exemplarily illustrated in FIG. 16. The function of the secondary frame wire 113 is to apply a predesigned orthodontic force to a tooth 108 or a group of teeth 108. The secondary frame wire 113 is configured in a loop configuration as a loop wire 110, or in a spiral configuration as a spiral wire 111, or in a mesh configuration as a mesh wire 112 as exemplarily illustrated in FIGS. 3A-3D. The primary frame wire 109 provides an anchoring force for each of the secondary frame wires 113. The loop wire 110 and the spiral wire 111 are positioned around individual tooth 108 and provide an individualized orthodontic force to each tooth independent of the orthodontic force applied to other teeth 108. Each tooth can receive and respond individually to an orthodontic force. Since teeth alignment treatments require individualized orthodontic forces and movement, each tooth must be segregated in its rigidity, anchors, and motion individually and receive an individualized orthodontic force. Furthermore, each tooth has six degrees of freedom, three spatial dimensions of translation, rotation, tipping, and torques. The secondary frame wires 113 can be designed around each tooth to allow relative motions between each tooth. Each of the secondary frame wires 113 remains rigid around each tooth and allows relative movement such as rotation, tipping, and torque between surrounding teeth 108.

The secondary frame wires 113 configured as the loop wire 110, the spiral wire 111, and the mesh wire 112 exert forces over a large planar surface. These secondary frame wires 113 can be bent and shaped around each tooth to provide a rigid anchor and coverage. In an embodiment, the secondary frame wires 113 are added as a mini-framework anchoring around the tooth or soldered to the primary frame wire 109. In another embodiment, the secondary frame wires 113 are added between the teeth 108 on a mesial side or a distal side of the tooth 108, or on a single tooth 108 on the lingual surface 108a or a facial surface 108b of posterior teeth 108. In an embodiment, the secondary frame wires 113 integrate and are interlocked with the enclosing layers 107 and offer a rigid anchor on each tooth surface. An embodiment of the secondary frame wire 113 in a mesh configuration as a mesh wire 112 in different shapes are exemplarily illustrated in FIGS. 15A-15C.

Figure 3B:
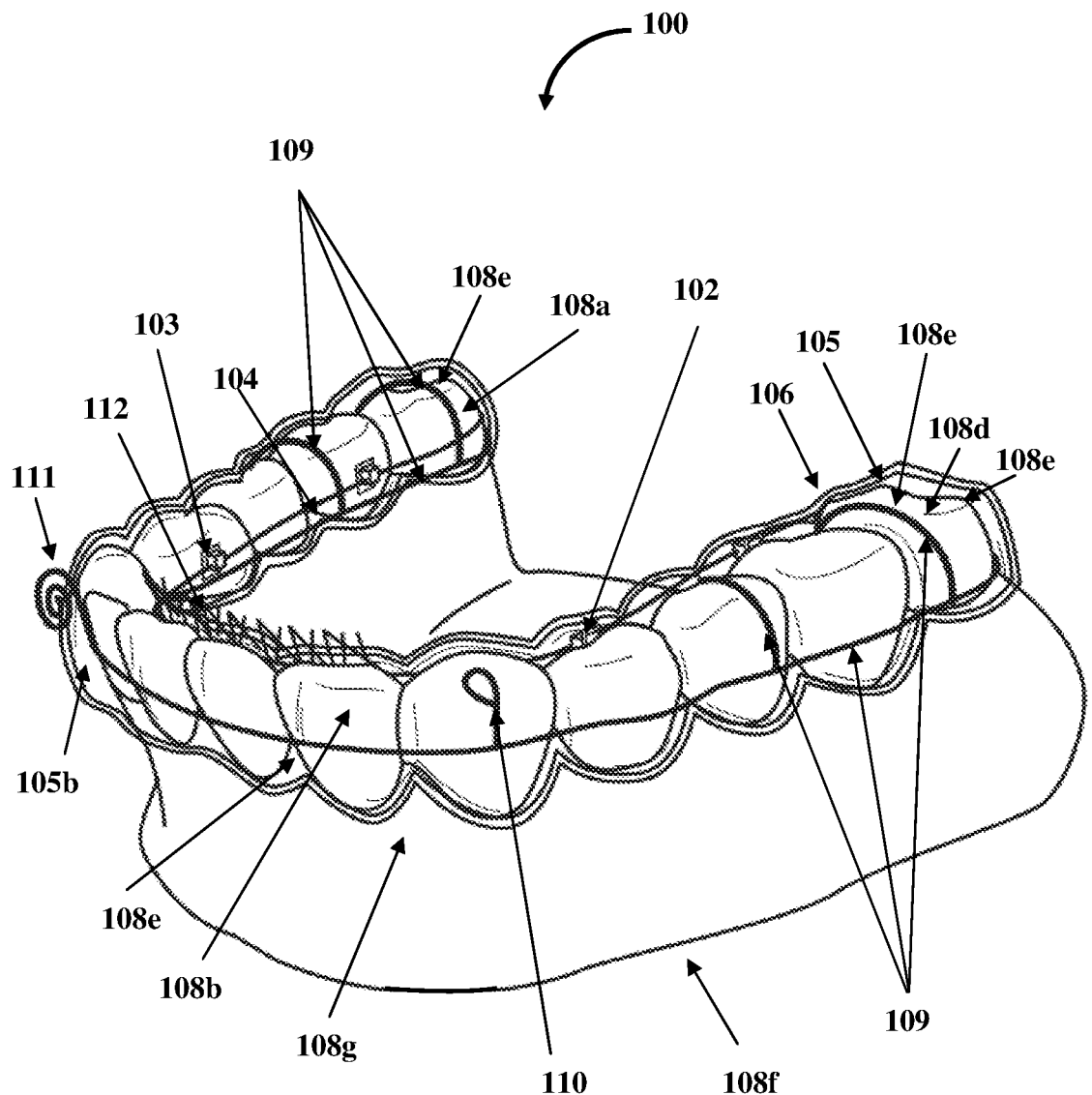
FIG. 3B exemplarily illustrates an assembled right isometric view of the removable orthodontic appliance comprising the embodiment of the detachable orthodontic bracket and wire system showing in FIG. 3A, positioned on teeth of a lower jaw.
Figure 3C:
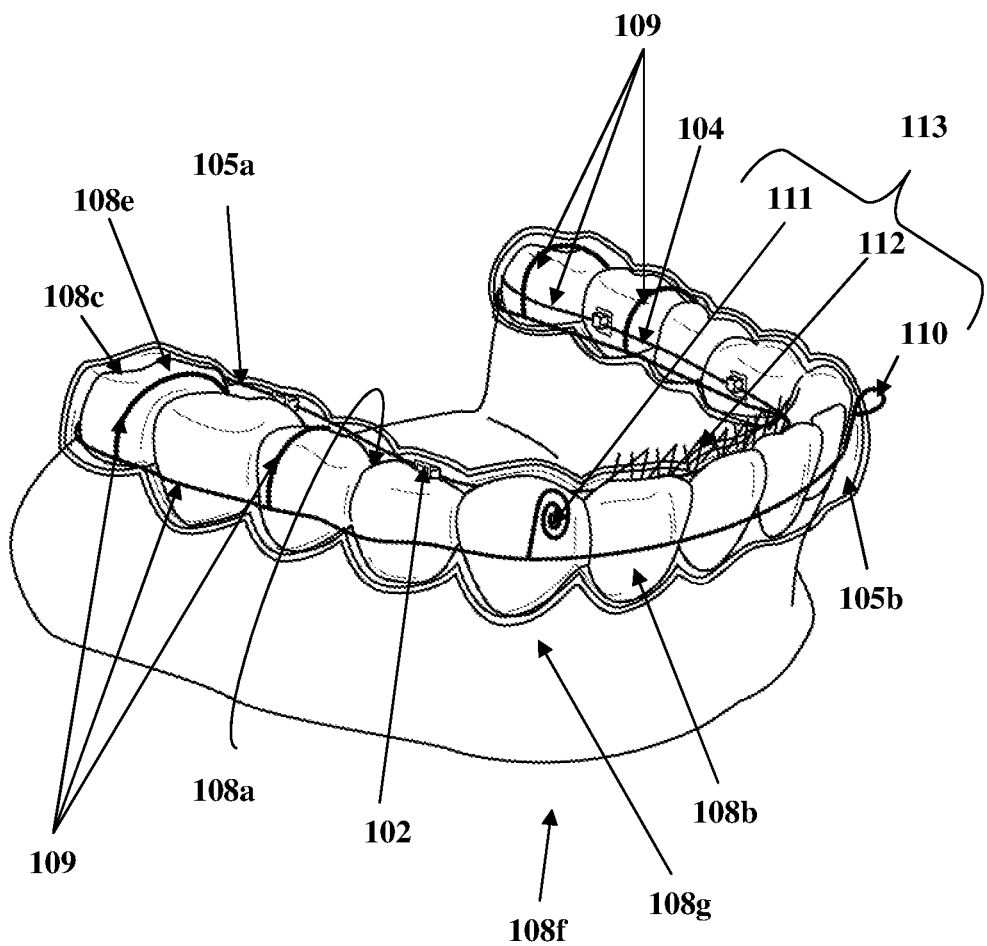
FIG. 3C exemplarily illustrates an assembled left isometric view of the removable orthodontic appliance comprising the embodiment of the detachable orthodontic bracket and wire system showing in FIG. 3A, positioned on teeth of a lower jaw.
Figure 3D:
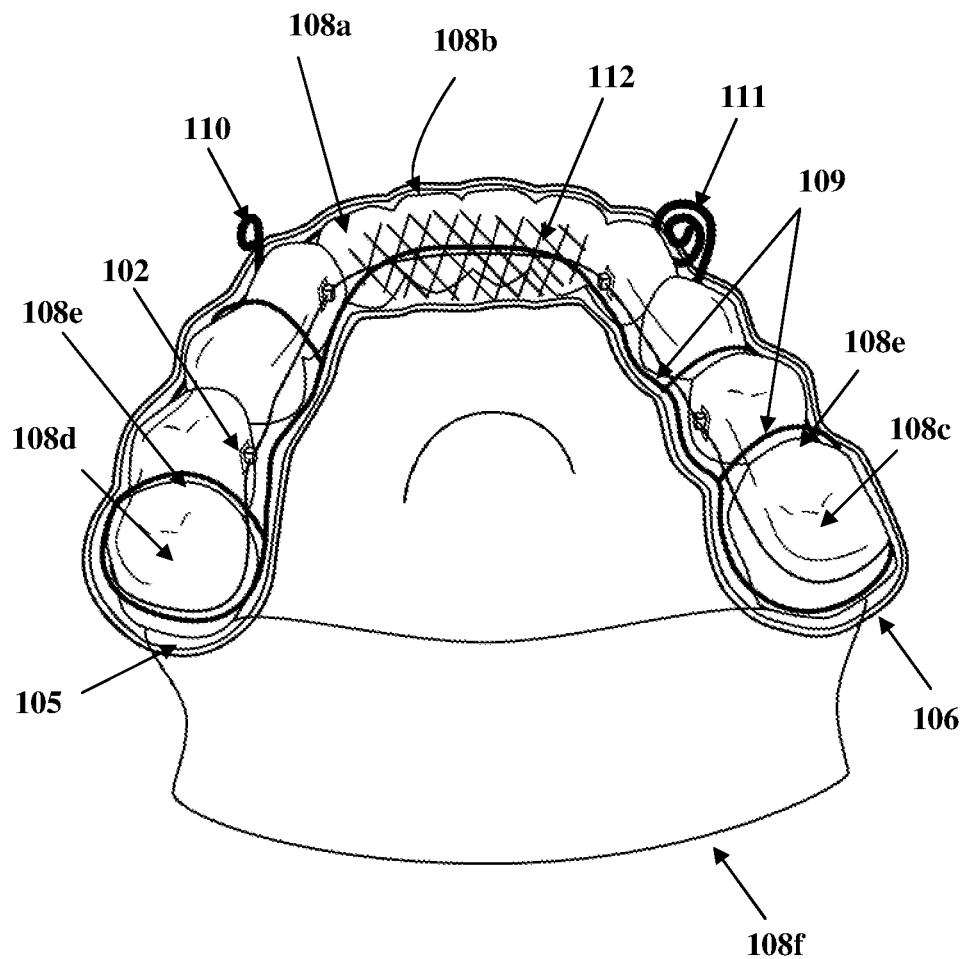
FIG. 3D exemplarily illustrates an assembled top perspective view of the removable orthodontic appliance comprising the embodiment of the detachable orthodontic bracket and wire system showing in FIG. 3A, positioned on teeth of a lower jaw.

FIG. 3B-3D exemplarily illustrate an assembled right isometric view, an assembled left isometric view, and an assembled top perspective view of the removable orthodontic appliance 100 respectively, comprising the embodiment of the detachable orthodontic bracket and wire system 101 shown in FIG. 3A, positioned on the teeth 108 of the lower jaw 108f. In this embodiment, the detachable orthodontic bracket and wire system 101 comprising the bracket bases 102, the brackets 103, the arch wire 104, the primary frame wire 109, the secondary frame wire 113, and the enclosing layers 107 constitute the arch tray, herein referred to as the "removable orthodontic appliance". The primary frame wire 109 with the secondary frame wires 113 is positioned on the interface of the teeth 108 and gums of the teeth 108. In an embodiment, the primary frame wire 109 with the secondary frame wires 113 is positioned on the teeth 108. In this embodiment, the detachable orthodontic bracket and wire system 101 comprising the bracket bases 102, the brackets 103, the arch wire 104, the primary frame wire 109, and the secondary frame wire 113 exemplarily illustrated in FIG. 3A, are embedded in the enclosing layers 107 via heat infusion as disclosed in the detailed description of FIG. 2.

The enclosing layers 107 hold the wires 104, 109, 110, 111, 112, etc., of the detachable orthodontic bracket and wire system 101 that constitute a metal framework that provides a holding force and a clear and esthetic appearance in frontal area of the teeth 108. In an embodiment, the enclosing layers 107 are added both on the top and bottom of the removable orthodontic appliance 100 to sandwich the detachable orthodontic bracket and wire system 101 comprising the bracket bases 102, the brackets 103, and the wires, for example, 104, 109, 110, 111, 112, etc., between the two enclosing layers 107. The top enclosing layer 106 is rigid to provide protection and the bottom enclosing layer 105 is flexible for ease and comfort of fitting onto the teeth 108. In an embodiment, the enclosing layers 107 are positioned over a bite surface of the removable orthodontic appliance 100 to guide the upper jaw (not shown) and the lower jaw 108f to move against each other to correct a cross bite, an over bite, an under bite, and other parafunctional relations between the upper jaw and the lower jaw 108f. In an embodiment, the plastic material of the enclosing layers 107 is bonded with the brackets 103 and the wires, for example, 104, 109, 110, 111, 112, etc. The brackets 103 and the wires, for example, 104, 109, 110, 111, 112, etc., are embedded inside a plastic material of the enclosing layers 107 via heat infusion. The wires, for example, the arch wire 104, the primary frame wire 109, and the secondary frame wires 113, etc., are configured to maximize the liquid flow of viscous melted plastic to each void between the teeth 108 and the wires, for example, 104, 109, 110, 111, 112, etc.

The physical properties and strength of the enclosing layers 107 made of, for example, a plastic material that can be changed at different stages during an orthodontic treatment and at different arches of the orthodontic treatment, as different amounts of force can be prescribed by a clinician on different teeth 108. For example, since translation needs a strong force, when a translation motion is the dominant motion of the teeth 108 along the primary frame wire 109 exemplarily illustrated in FIG. 3A, a strong arch wire 104 and a rigid plastic material are used. Softer plastics, for example, polyethylene can be used for the enclosing layers 107 when more elastic force is needed to pull the teeth 108 together. Materials such as Zendura® of Bay Materials LLC offer both rigidity and resilience and can be used on the enclosing layers 107, when moderate level forces are needed. The thickness of the plastic material used can be thin, for example, about 0.5 mm to about 2 mm so that the plastic material offers elasticity to fit the removable orthodontic appliance 100 onto the teeth 108, while the wires, for example, 104, 109, 110, 111, 112, etc., retain their elasticity.

Figure 4A:
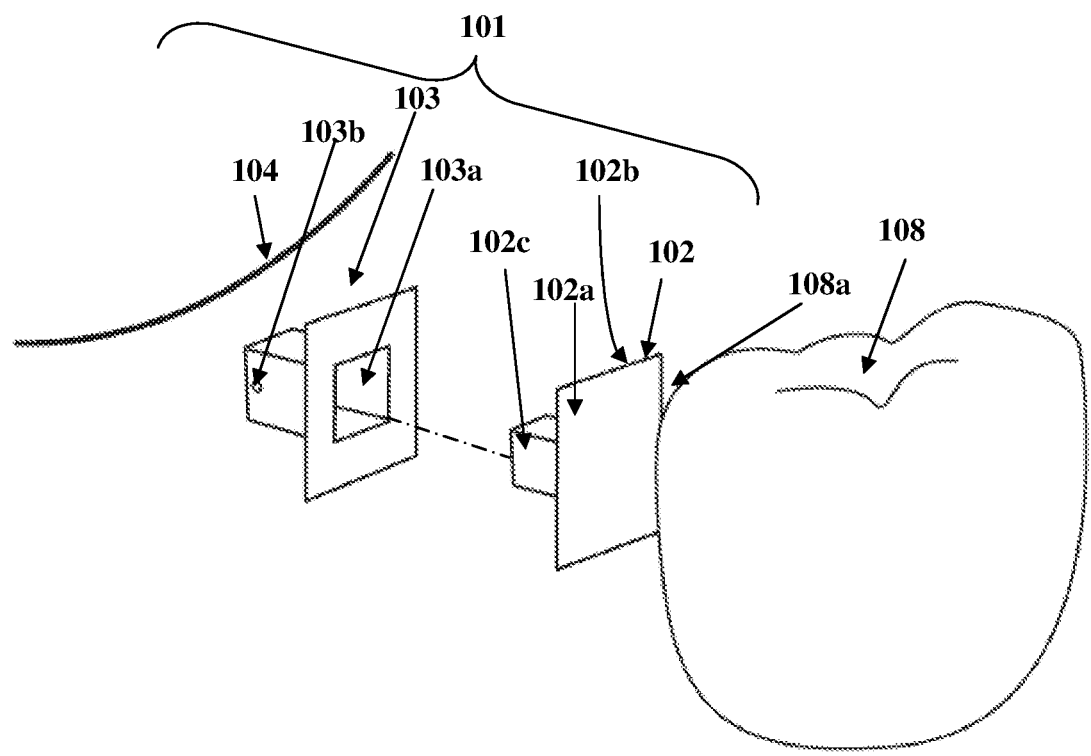
FIG. 4A exemplarily illustrates an exploded view of the detachable orthodontic bracket and wire system.
Figure 4B:
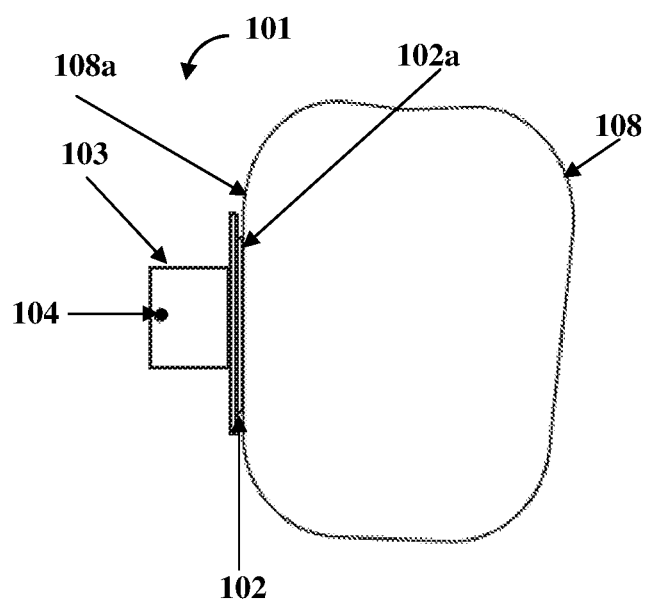
FIG. 4B exemplarily illustrates an assembled left side elevation view of the detachable orthodontic bracket and wire system.

FIGS. 4A-4B exemplarily illustrate an exploded view and an assembled left side elevation view respectively, of the detachable orthodontic bracket and wire system 101 exemplarily illustrated in FIG. 1 and FIG. 3A. Each bracket 103 of the detachable orthodontic bracket and wire system 101 comprises the slot channel 103b passing through the bracket 103 as exemplarily illustrated in FIG. 4A. As exemplarily illustrated in FIGS. 4A-4B, the slot channel 103b has a circular cross section. Each bracket 103 of the detachable orthodontic bracket and wire system 101 is positioned such that the slot channel 103b of each bracket 103 is positioned proximal to the inner lingual side 105a of the first soft enclosing layer 105 exemplarily illustrated in FIG. 1 and FIG. 3A. In an embodiment (not shown), the slot channel 103b of each bracket 103 is positioned proximal to the inner facial side 105b of the first soft enclosing layer 105. As exemplarily illustrated in FIG. 4B, the arch wire 104 is accommodated within the slot channel 103b of each bracket 103 on the lingual surface 108a of the teeth 108 exemplarily illustrated in FIG. 1, FIG. 2, and FIGS. 3A-3D. The arch wire 104 has a circular cross section as exemplarily illustrated in FIGS. 4A-4B, and is inserted into the slot channel 103b having a circular cross section. The arch wire 104 engages with the bracket 103 in the slot channel 103b of the bracket 103 that is spatially separated from the bracket base 102. The separation can be vertical or horizontal. The arch wire 104 has common arch forms, for example, a round tapered arch form, an oval shaped arch form, etc. Unlike the arch wire 104 positioned on the facial surface 108b of the teeth 108, in an embodiment, the arch wire 104 positioned on the lingual surface 108a of the teeth 108 has a twist or a twisted arch form at a canine area of the teeth 108 and a uniform arch form in other regions of the teeth 108. As the first soft enclosing layer 105 exemplarily illustrated in FIG. 1, FIG. 2, and FIGS. 3A-3D, reduces orthodontic strength of the arch wire 104, an arch wire 104 with a high strength or a large diameter is used to compensate the loss of orthodontic forces.

As exemplarily illustrated in FIGS. 4A-4B, the bracket 103 further comprises a second interlocking element 103a, for example, a cuboidal receptacle, and the bracket base 102 comprises a first interlocking element 102c, for example, a cuboidal projection extending from the second surface 102b of the bracket base 102. The second interlocking element 103a of the bracket 103 is configured to accommodate the first interlocking element 102c of the bracket base 102. The first interlocking element 102c of the bracket base 102 interlocks with the second interlocking element 103a of the bracket 103 as exemplarily illustrated in FIG. 4B. In an embodiment, the first interlocking element 102c of the bracket base 102 snap fits into the second interlocking element 103a of the bracket 103. In an embodiment, the arch wire 104 and the brackets 103 are coated with a polymeric material, for example, a polyurethane resin formulated for rigidly bonding the arch wire 104 and each of the brackets 103 to the first soft enclosing layer 105, or to both the enclosing layers 107 using one or more infusion methods, for example, electric heating, microwave heating, etc.

Figure 4C:
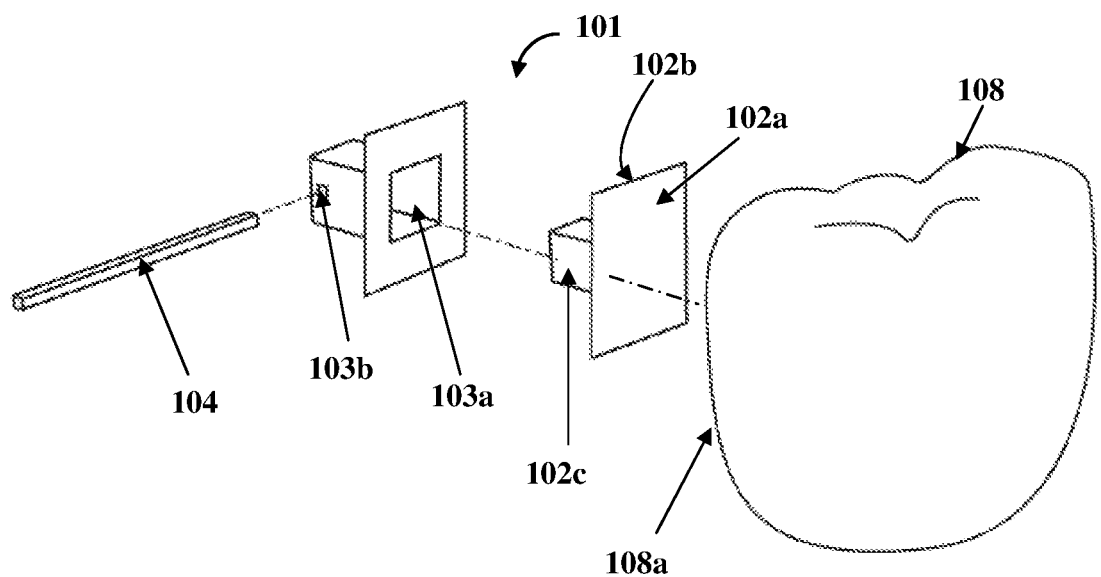
FIG. 4C exemplarily illustrates an exploded view of an embodiment of the detachable orthodontic bracket and wire system, showing a slot channel of a bracket and an arch wire with a rectangular cross section.
Figure 4D:
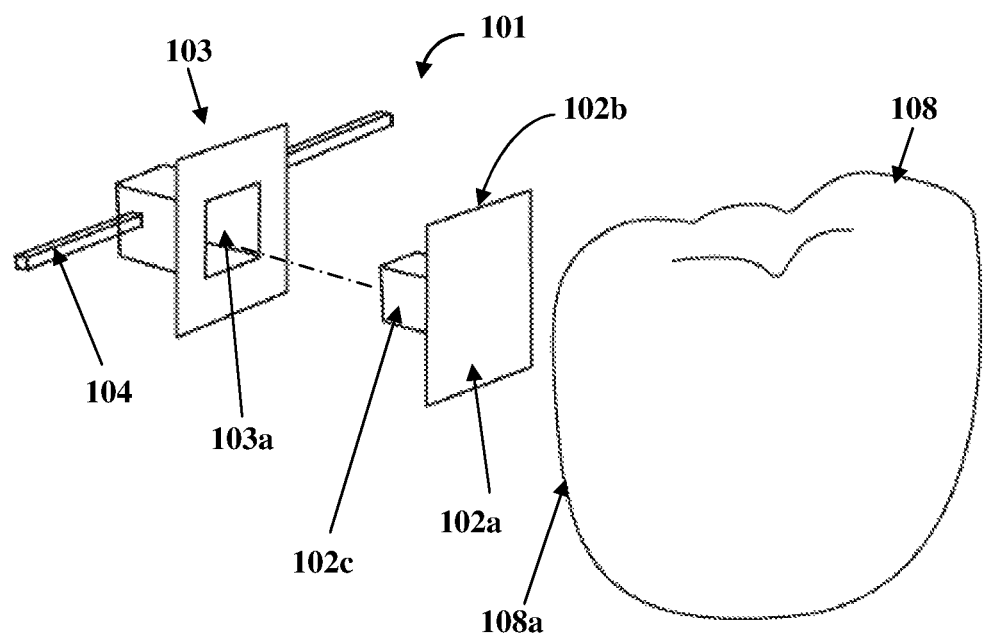
FIG. 4D exemplarily illustrates an exploded view of the embodiment of the detachable orthodontic bracket and wire system shown in FIG. 4C, showing the arch wire with a rectangular cross section inserted into the slot channel with a rectangular cross section.

FIGS. 4C-4D exemplarily illustrate exploded views of an embodiment of the detachable orthodontic bracket and the wire system 101, showing the slot channel 103b of the bracket 103 and an arch wire 104 with a rectangular cross section. The slot channel 103b with the rectangular cross section exemplarily illustrated in FIG. 4C, is configured to accommodate the arch wire 104 with the rectangular cross section. The arch wire 104 with the rectangular cross section is inserted into the slot channel 103b with the rectangular cross section as exemplarily illustrated in FIG. 4D.

Figure 5A:
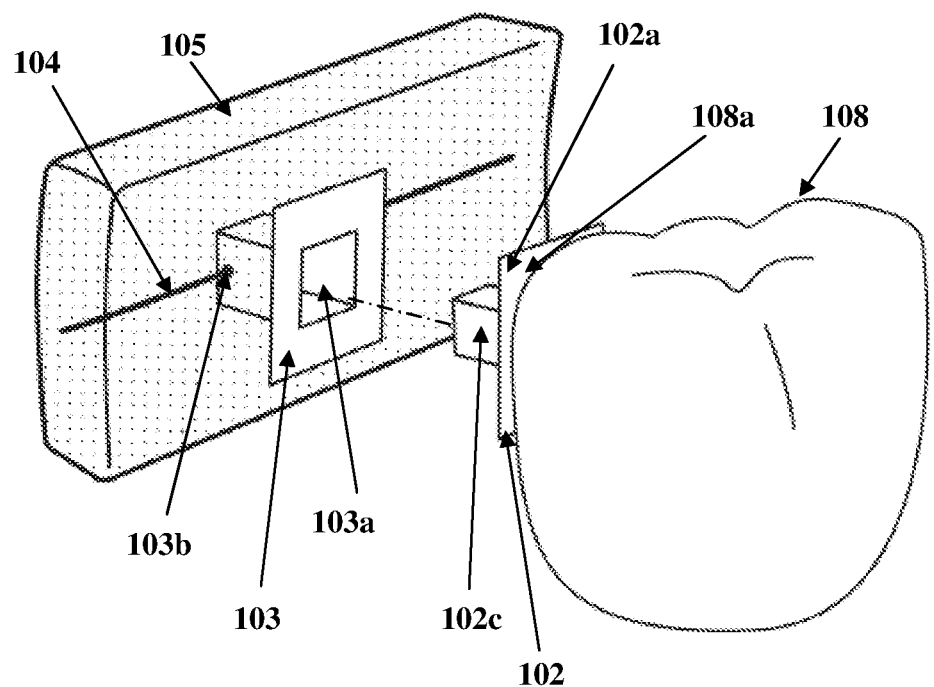
FIG. 5A exemplarily illustrates an exploded view of the detachable orthodontic bracket and wire system, showing the bracket and the arch wire infused in an enclosing layer of the removable orthodontic appliance.
Figure 5B:
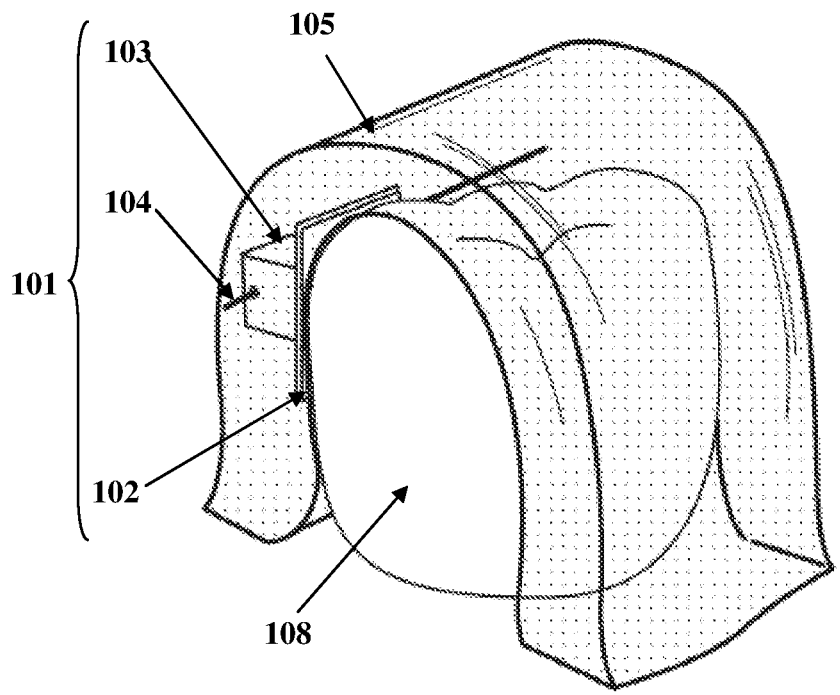
FIG. 5B exemplarily illustrates an assembled perspective view of the detachable orthodontic bracket and wire system, showing the bracket and the arch wire infused in the enclosing layer of the removable orthodontic appliance.

FIGS. 5A-5B exemplarily illustrate an exploded view and an assembled perspective view respectively, of the detachable orthodontic bracket and wire system 101 exemplarily illustrated in FIG. 1 and FIG. 3A, showing the bracket 103 and the arch wire 104 infused in the first soft enclosing layer 105 of the removable orthodontic appliance 100 exemplarily illustrated in FIG. 1 and FIG. 3A. The first surface 102a of each bracket base 102 is rigidly attached or bonded to the lingual surface 108a of the teeth 108. A first interlocking element 102c, for example, a square shaped projection is attached to and extends from the second surface 102b of the bracket base 102. Each corresponding bracket 103 comprises a second interlocking element 103a, for example, a square shaped receptacle configured to receive and interlock with the square shaped projection of the bracket base 102. Detachably interlocking the square shaped projection of the bracket base 102 into the square shaped receptacle of the bracket 103 allows detachable attachment of the bracket 103 to the bracket base 102, and in turn, removable attachment of the removable orthodontic appliance 100 to the lingual surface 108a of the teeth 108. The arch wire 104 passes through the slot channel 103b of each bracket 103 as exemplarily illustrated in FIGS. 5A-5B. The bracket 103 with the arch wire 104 inserted in the slot channel 103b, is infused and embedded into the first soft enclosing layer 105 as exemplarily illustrated in FIGS. 5A-5B, thereby enabling the removable orthodontic appliance 100 to be removably attached to the lingual surface 108a of the teeth 108.

Figure 6A:
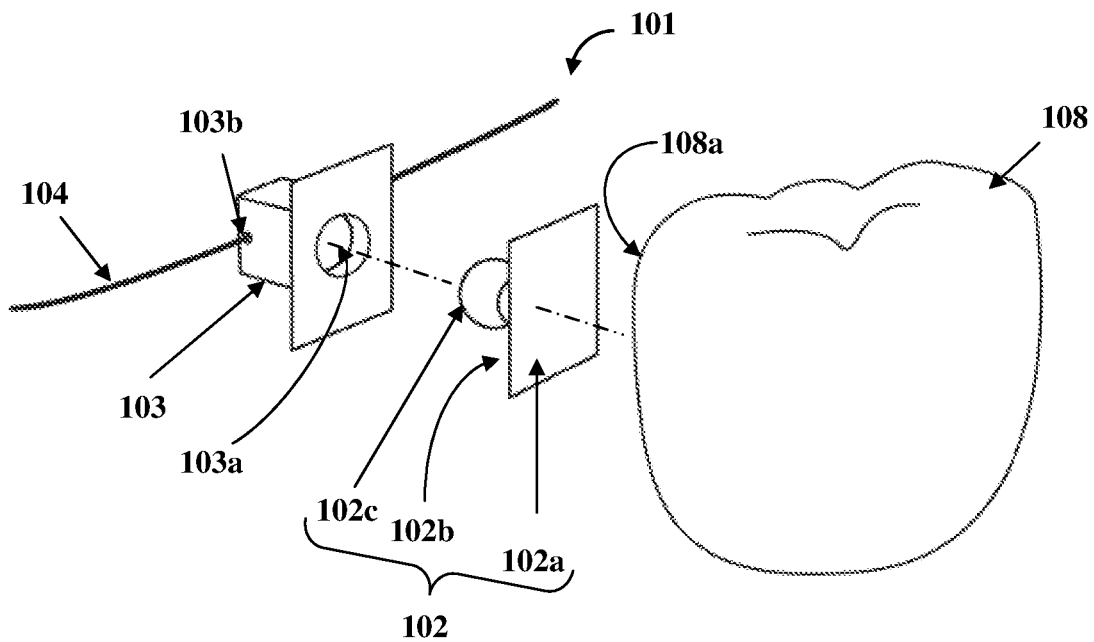
FIGS. 6A-6B exemplarily illustrate exploded views of an embodiment of the detachable orthodontic bracket and wire system, showing a first embodiment of the bracket detached from an embodiment of the bracket base.
Figure 6B:
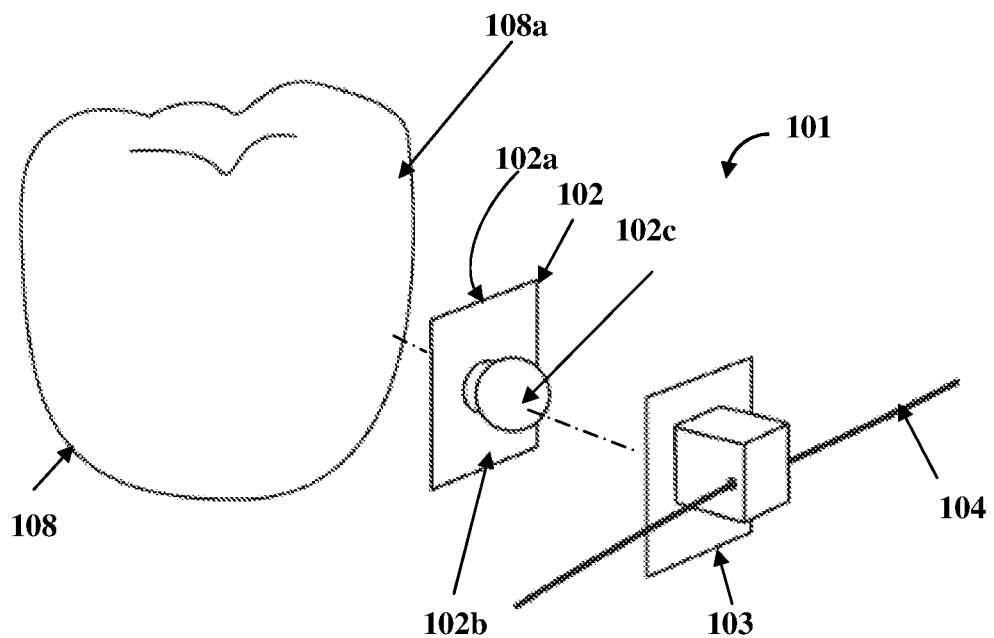

FIGS. 6A-6B exemplarily illustrate exploded views of an embodiment of the detachable orthodontic bracket and wire system 101 exemplarily illustrated in FIG. 1 and FIG. 3A, showing a first embodiment of the bracket 103 detached from an embodiment of the bracket base 102. In an embodiment, the first interlocking element 102c of the bracket base 102 is configured, for example, as a ball projection that is attached to and extends from the second surface 102b of the bracket base 102. In this embodiment, the second interlocking element 103a of the bracket 103 is configured, for example, as a socket to receive and interlock with the ball projection of the bracket base 102. The ball projection of the bracket base 102 interlocks with the second interlocking element 103a, for example, the socket of the bracket 103 to attach the bracket 103 to the bracket base 102. The ball projection of the bracket base 102 snaps into the socket of the bracket 103 to provide better retention. To snap into the socket of the bracket 103, the ball projection 102c of the bracket base 102 is compressible and therefore passes through the socket of the bracket 103 and then locks into the socket of the bracket 103.

In an embodiment (not shown), the second interlocking element 103a is configured, for example, as a ball projection that is attached to and extends from the bracket 103. In this embodiment, the first interlocking element 102c of the bracket base 102 is configured, for example, as a socket to receive and interlock with the ball projection of the bracket 103. The ball projection of the bracket 103 snaps into the socket of the bracket base 102 to provide better retention. For purposes of illustration, the detailed description refers to a ball projection and socket interlocking mechanism for attaching the bracket 103 to the bracket base 102; however the scope of the detachable orthodontic bracket and wire system 101 disclosed herein and exemplarily illustrated in FIG. 1 and FIG. 3A, is not limited to a ball projection and socket interlocking mechanism but may be extended to include any interlocking mechanism that detachably attaches the bracket 103 to the bracket base 102.

Figure 7A:
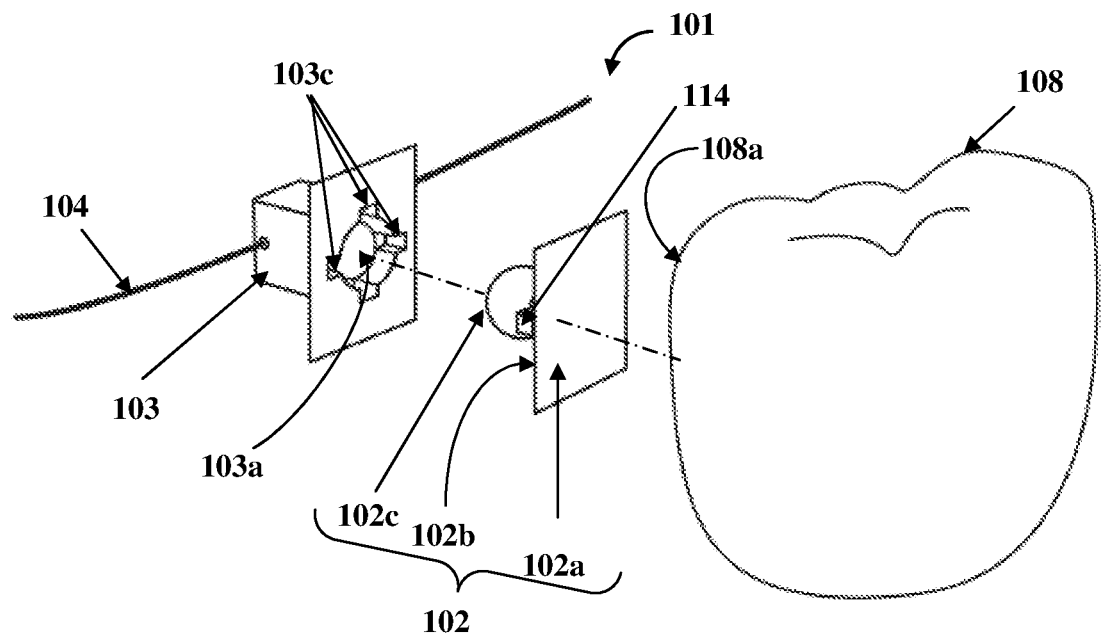
FIGS. 7A-7B exemplarily illustrate exploded views of an embodiment of the detachable orthodontic bracket and wire system, showing a second embodiment of the bracket detached from an embodiment of the bracket base with a cross bar.
Figure 7B:
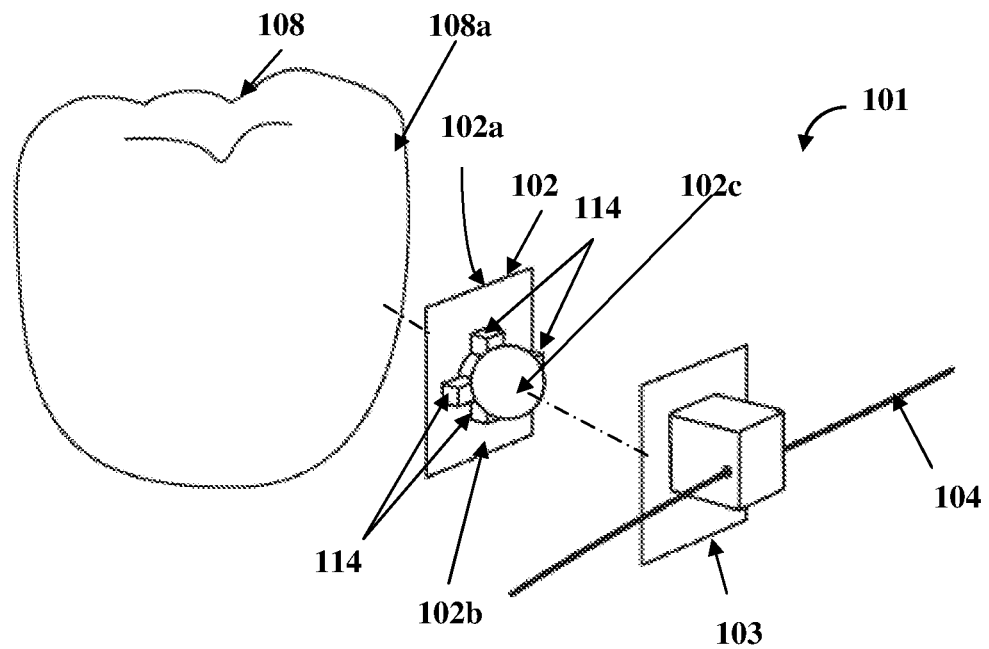

FIGS. 7A-7B exemplarily illustrate exploded views of an embodiment of the detachable orthodontic bracket and wire system 101 exemplarily illustrated in FIG. 1 and FIG. 3A, showing a second embodiment of the bracket 103 detached from an embodiment of the bracket base 102 with a cross bar 114. Since the first interlocking element 102c, for example, the ball projection does not offer retention against rotation around a ball axis, an additional structure is needed to engage the bracket 103 with the bracket base 102. In an embodiment, the detachable orthodontic bracket and wire system 101 exemplarily illustrated in FIG. 1 and FIG. 3A, further comprises the cross bar 114 positioned below each first interlocking element 102c, for example, each ball projection of each bracket base 102. In this embodiment, each bracket 103 further comprises a receptacle 103c to engage the cross bar 114 and restrict movement of each bracket 103 over a corresponding bracket base 102. As the socket of the bracket 103 snaps into the ball projection of the bracket base 102, the bracket 103 engages the bracket base 102 through the ball projection and the cross bar 114. If an orthodontic force is applied to rotate the bracket 103, the rotational force transfers from the bracket 103 to the bracket base 102 through the cross bar 114. Since the bracket bases 102 are bonded, for example, to the lingual surface 108a of the teeth 108 exemplarily illustrated in FIG. 1 and FIGS. 3A-3D, the orthodontic force from the bracket base 102 transfers to the teeth 108 with precision and efficiency.

Figure 7C:
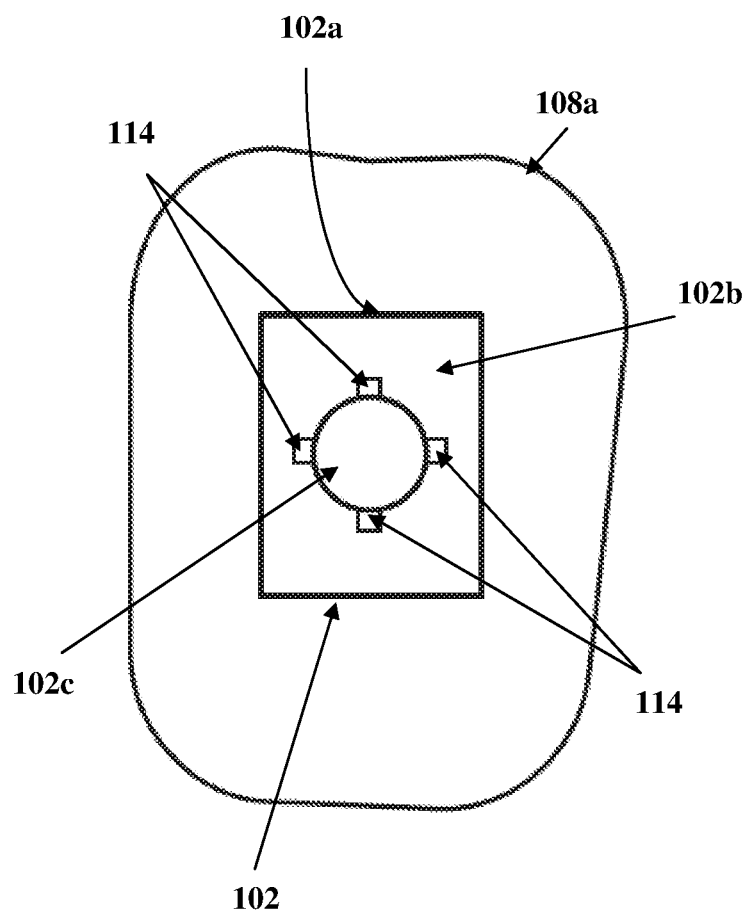
FIG. 7C exemplarily illustrates a front elevation view of the bracket base with the cross bar fixed to lingual surface of a tooth in the embodiment of the bracket base with the cross bar shown in FIGS. 7A-7B.

FIG. 7C exemplarily illustrates a front elevation view of the bracket base 102 with the cross bar 114 fixed to the lingual surface 108a of the tooth 108 in the embodiment of the bracket base 102 with the cross bar 114 shown in FIGS. 7A-7B. The cross bar 114 is positioned below each first interlocking element 102c on the second surface 102b of the bracket base 102. On engaging with the receptacle 103c, the cross bar 114 restricts movement of each bracket 103 over the corresponding bracket base 102 as exemplarily illustrated in FIGS. 7A-7B.

Figure 8A:
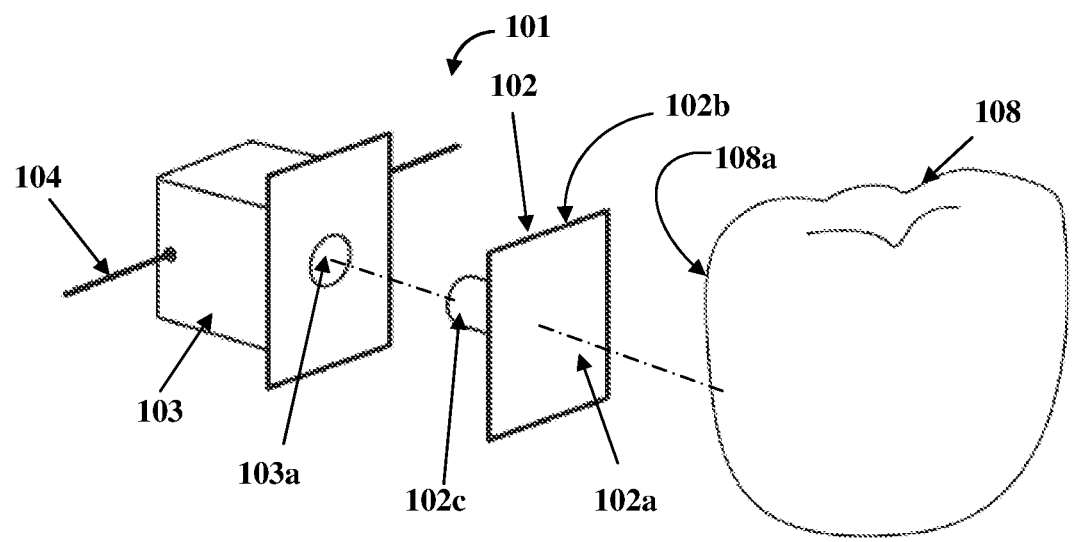
FIGS. 8A-8B exemplarily illustrate exploded views of an embodiment of the detachable orthodontic bracket and wire system, showing a third embodiment of the bracket detached from an embodiment of the bracket base.
Figure 8B:
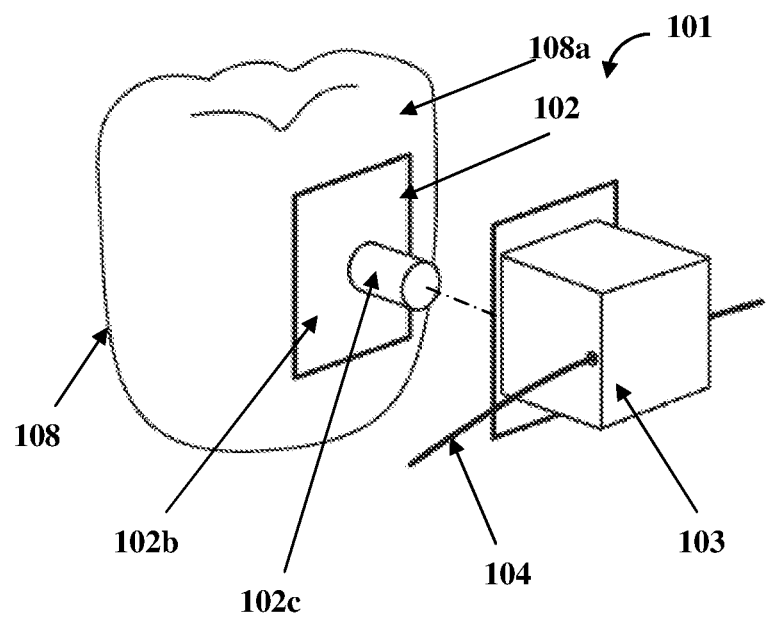

FIGS. 8A-8B exemplarily illustrate exploded views of an embodiment of the detachable orthodontic bracket and wire system 101 exemplarily illustrated in FIG. 1 and FIG. 3A, showing a third embodiment of the bracket 103 detached from an embodiment of the bracket base 102. In this embodiment, the bracket base 102 comprises a single first interlocking element 102c, for example, a single cylindrical shaped projection and the bracket 103 comprises a corresponding single second interlocking element 103a, for example, a single cylindrical shaped receptacle. The single cylindrical shaped projection of the bracket base 102 is attached to and extends from the second surface 102b of the bracket base 102. The single cylindrical shaped projection of the bracket base 102 interlocks with the single cylindrical shaped receptacle of the bracket 103 to attach the bracket 103 to the bracket base 102. The single cylindrical shaped projection of the bracket base 102 snaps into the single cylindrical shaped receptacle of the bracket 103 to provide better retention.

Figure 9A:
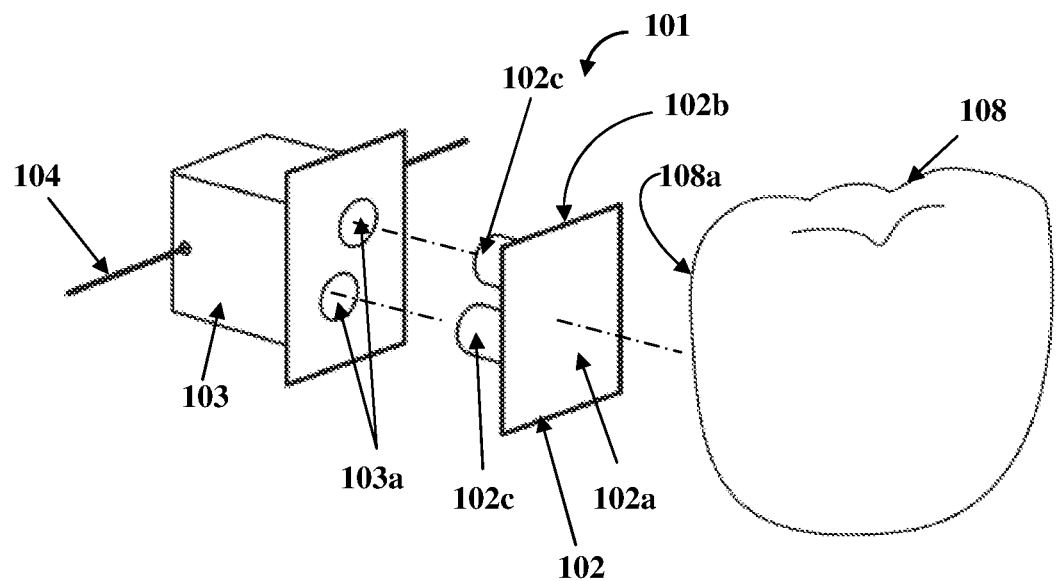
FIGS. 9A-9B exemplarily illustrate exploded views of an embodiment of the detachable orthodontic bracket and wire system, showing a fourth embodiment of the bracket detached from an embodiment of the bracket base.
Figure 9B:
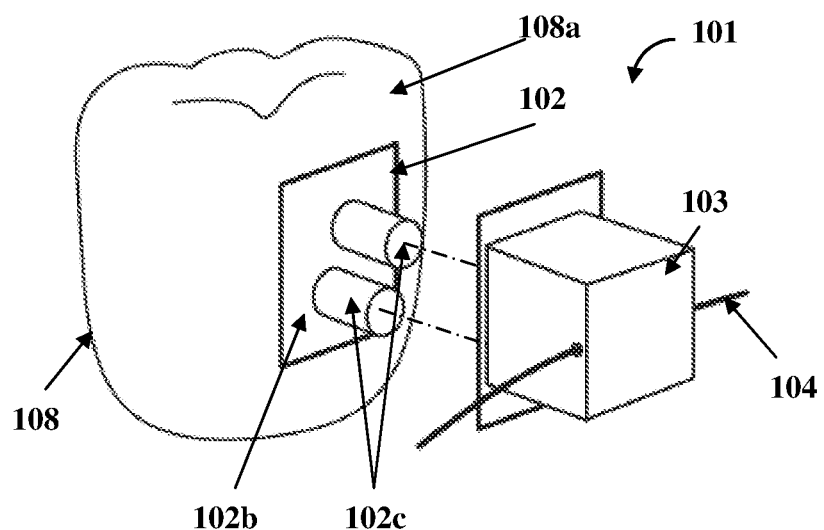

FIGS. 9A-9B exemplarily illustrate exploded views of an embodiment of the detachable orthodontic bracket and wire system 101 exemplarily illustrated in FIG. 1 and FIG. 3A, showing a fourth embodiment of the bracket 103 detached from an embodiment of the bracket base 102. In this embodiment, the bracket base 102 comprises two first interlocking elements 102c, for example, two cylindrical shaped projections and the bracket 103 comprises corresponding two second interlocking elements 103a, for example, two cylindrical shaped receptacles. The two cylindrical shaped projections of the bracket base 102 are attached to and extend from the second surface 102b of the bracket base 102. The two cylindrical shaped projections of the bracket base 102 interlock with the two cylindrical shaped receptacles of the bracket 103 to attach the bracket 103 to the bracket base 102. The two cylindrical shaped projections of the bracket base 102 snap into the two cylindrical shaped receptacles of the bracket 103 to provide better retention. Multiple cylindrical shaped projections are configured in the bracket base 102 to increase the rotational force of the bracket 103.

When there are multiple first interlocking elements 102c, for example, projections extending from the second surface 102b of the bracket base 102, it is difficult to insert all the first interlocking elements 102c into the corresponding second interlocking elements 103a of the bracket 103 at the same time. Therefore, one or more of the first interlocking elements 102c of the bracket base 102 can be used as guide points, the position of which will not be changed and which will insert into the corresponding second interlocking elements 103a of the bracket 103. The other of the first interlocking elements 102c of the bracket base 102 need to be arranged to push in a new position, since the change of position produces a reaction force that positions the teeth 108, to a new position. To produce the orthodontic force to move the teeth 108 from a current position to the new position, the second interlocking elements 103a of the brackets 103 and the first interlocking elements 102c of the bracket bases 102 are positioned at a predetermined location so that the change of position of the teeth 108 produces a reactive force to return to the original position. At the new positions of the teeth 108, the first interlocking elements 102c of the bracket bases 102 must fit into the corresponding second interlocking elements 103a of the brackets 103 as the first interlocking elements 102c have moved to a new position along with the teeth 108. To optimize the fitting process for dental providers, a primary first interlocking element 102c of each bracket base 102 is retained at the original position as an anchor and a guide, and fitting of the other first interlocking elements 102c of each bracket base 102 is executed relative to the primary first interlocking element 102c.

Figure 10A:
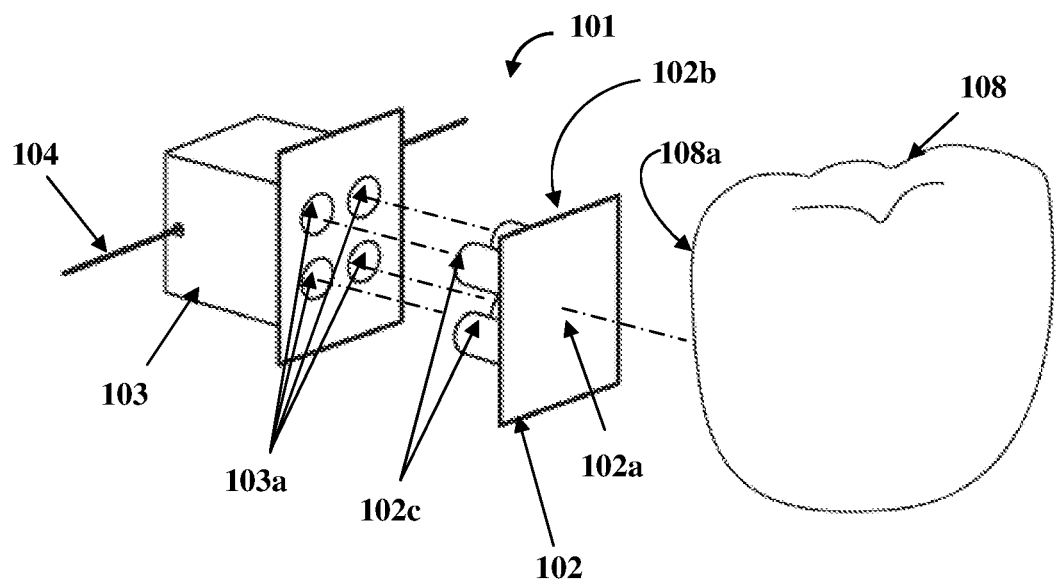
FIGS. 10A-10B exemplarily illustrate exploded views of an embodiment of the detachable orthodontic bracket and wire system, showing a fifth embodiment of the bracket detached from an embodiment of the bracket base.
Figure 10B:
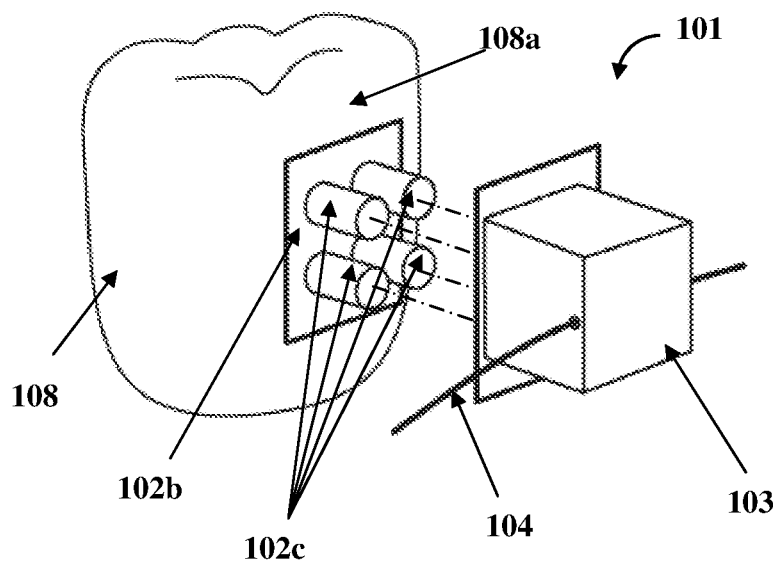

FIGS. 10A-10B exemplarily illustrate exploded views of an embodiment of the detachable orthodontic bracket and wire system 101 exemplarily illustrated in FIG. 1 and FIG. 3A, showing a fifth embodiment of the bracket 103 detached from an embodiment of the bracket base 102. In this embodiment, the bracket base 102 comprises four first interlocking elements 102c, for example, four cylindrical shaped projections and the bracket 103 comprises corresponding four second interlocking elements 103a, for example, four cylindrical shaped receptacles. The four cylindrical shaped projections of the bracket base 102 are attached to and extend from the second surface 102b of the bracket base 102. The four cylindrical shaped projections of the bracket base 102 interlock with the four cylindrical shaped receptacles of the bracket 103 to attach the bracket 103 to the bracket base 102. The four cylindrical shaped projections of the bracket base 102 snap into the four cylindrical shaped receptacles of the bracket 103 to provide better retention.

Figure 11A:
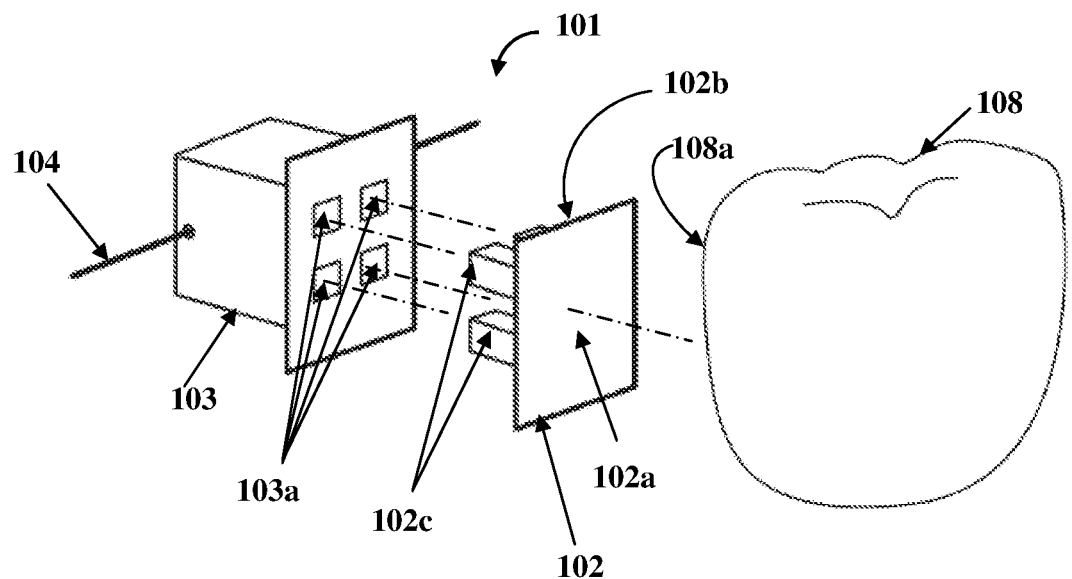
FIGS. 11A-11B exemplarily illustrate exploded views of an embodiment of the detachable orthodontic bracket and wire system, showing a sixth embodiment of the bracket detached from an embodiment of the bracket base.
Figure 11B:
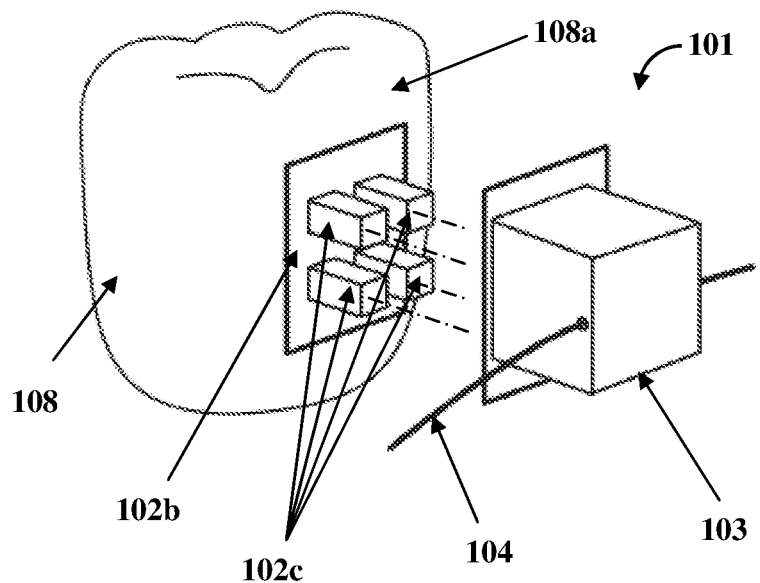

FIGS. 11A-11B exemplarily illustrate exploded views of an embodiment of the detachable orthodontic bracket and wire system 101 exemplarily illustrated in FIG. 1 and FIG. 3A, showing a sixth embodiment of the bracket 103 detached from an embodiment of the bracket base 102. In this embodiment, the bracket base 102 comprises four first interlocking elements 102c, for example, four rectangular or cuboidal shaped projections and the bracket 103 comprises corresponding four second interlocking elements 103a, for example, four rectangular or cuboidal shaped receptacles. The four rectangular or cuboidal shaped projections of the bracket base 102 are attached to and extend from the second surface 102b of the bracket base 102. The four rectangular or cuboidal shaped projections of the bracket base 102 interlock with the four rectangular or cuboidal shaped receptacles of the bracket 103 to attach the bracket 103 to the bracket base 102. The four rectangular or cuboidal shaped projections of the bracket base 102 snap into the four rectangular or cuboidal shaped receptacles of the bracket 103 to provide better retention.

FIG. 12A exemplarily illustrates a disassembled partial sectional view of an embodiment of the detachable orthodontic bracket and wire system 101 exemplarily illustrated in FIG. 1 and FIG. 3A, showing positioning of a first interlocking element 102c, for example, a ball projection in a direction substantially perpendicular to the second surface 102b of the bracket base 102 positioned on a lingual surface 108a of the teeth 108. The ball projection is positioned substantially perpendicular with respect to the second surface 102b of the bracket base 102. The bracket 103 is infused in the first soft enclosing layer 105, while the second hard enclosing layer 106 is positioned over the first soft enclosing layer 105. As exemplarily illustrated in FIG. 12A, the bracket 103 comprising the second interlocking element 103a, for example, the socket is detached from the ball projection of the bracket base 102.

FIG. 12B exemplarily illustrates an assembled partial sectional view of the embodiment of the detachable orthodontic bracket and wire system 101 exemplarily illustrated in FIG. 1 and FIG. 3A, showing attachment of the bracket 103 to the bracket base 102 shown in FIG. 12A, in a direction substantially perpendicular to the second surface 102b of the bracket base 102. As exemplarily illustrated in FIG. 12B, the bracket 103 comprising the second interlocking element 103a, for example, a socket exemplarily illustrated in FIG. 12A, is attached to the bracket base 102 comprising the interlocking element 102c, for example, the ball projection positioned in a direction substantially perpendicular to the second surface 102b of the bracket base 102 exemplarily illustrated in FIG. 12A.

FIG. 13A exemplarily illustrates a disassembled partial sectional view of an embodiment of the detachable orthodontic bracket and wire system 101 exemplarily illustrated in FIG. 1 and FIG. 3A, showing the positioning of the first interlocking element 102c, for example, a ball projection in a direction substantially parallel to the second surface 102b of the bracket base 102. The bracket 103 is infused in the first soft enclosing layer 105, while the second hard enclosing layer 106 is positioned over the first soft enclosing layer 105. In an embodiment, the ball projection is positioned substantially parallel with respect to the second surface 102b of the bracket base 102. To optimally control the orthodontic force, the alignment of the ball projection is changed from substantially perpendicular to the tooth surface to substantially parallel to the tooth surface. The parallel alignment of the ball projection allows easier insertion and engagement of the detachable orthodontic bracket and wire system 101 exemplarily illustrated in FIG. 1, from the top of the teeth 108. The parallel alignment of the ball projection provides rotational force around the tooth axis. In another embodiment, the ball projection is positioned at any angle, for example, from about 90° to about 0° with respect to the second surface 102b of the bracket base 102 to optimize the insertion process. As exemplarily illustrated in FIG. 13A, the bracket 103 comprising, for example, the socket is detached from the ball projection of the bracket base 102.

FIG. 13B exemplarily illustrates an assembled partial sectional view of the embodiment of the detachable orthodontic bracket and wire system 101 exemplarily illustrated in FIG. 1 and FIG. 3A, showing attachment of the bracket 103 to the bracket base 102 shown in FIG. 13A, in a direction substantially parallel to the second surface 102b of the bracket base 102. As exemplarily illustrated in FIG. 13B, the bracket base 102 comprising the first interlocking element 102c, for example, a ball projection positioned in a direction substantially parallel to the second surface 102b of the bracket base 102 is attached to the socket of the bracket 103.

Figure 14:
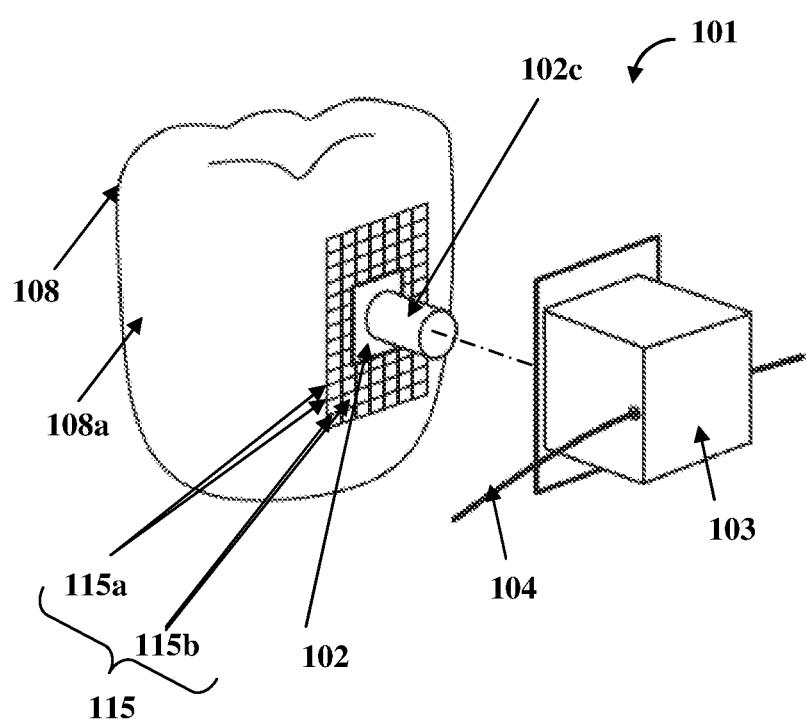
FIG. 14 exemplarily illustrates an embodiment of the detachable orthodontic bracket and wire system, showing a mesh element attached to the bracket base.

FIG. 14 exemplarily illustrates an embodiment of the detachable orthodontic bracket and wire system 101 exemplarily illustrated in FIG. 1 and FIG. 3A, showing a mesh element 115 attached to the bracket base 102. In this embodiment, the bracket 103 is attached to the bracket base 102 that is secured to the mesh element 115. The mesh element 115 comprises mesh work 115a with holes 115b to allow the plastic material of the first soft enclosing layer 105 exemplarily illustrated in FIG. 1 and FIG. 3A, to run through the holes 115b and secure each bracket base 102 to the first soft enclosing layer 105. In an embodiment, the mesh element 115 conforms to a shape of the lingual surface 108a of the teeth 108 exemplarily illustrated in FIG. 1 and FIGS. 3A-3D. The mesh element 115 provides a rigid yet elastic anchor to the lingual surface 108a of the teeth 108 exemplarily illustrated in FIG. 1 and FIGS. 3A-3D. The mesh element 115 is soldered or welded to the bracket base 102. In an embodiment, the mesh element 115 conforms to the shape of the teeth 108 and is positioned on each bracket base 102 around the first interlocking element 102c to secure each bracket base 102 to the first soft enclosing layer 105.

Figure 15A:
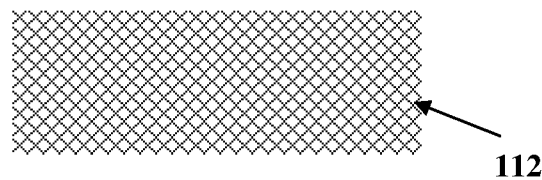
FIGS. 15A-15C exemplarily illustrate elevation views of embodiments of a secondary frame wire of the embodiment of the detachable orthodontic bracket and wire system shown in FIG. 3A.
Figure 15B:
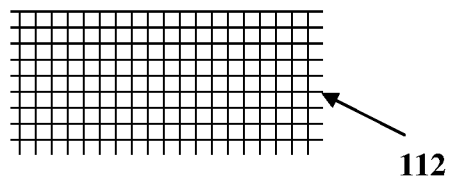
Figure 15C:
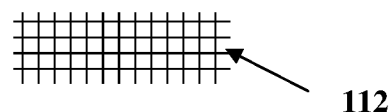

FIGS. 15A-15C exemplarily illustrate elevation views of embodiments of a secondary frame wire 113 of the embodiment of the detachable orthodontic bracket and wire system 101 shown in FIG. 3A. FIG. 15A exemplarily illustrates an embodiment of the mesh wire 112 configured, for example, as a cross bar mesh. The mesh wire 112 configured as a cross bar mesh offers different directions of elastic force along the mesh configuration. In an embodiment, a thin stripe of the mesh wire 112 configured as a cross bar mesh is positioned on the lingual side 105a of the first soft enclosing layer 105 exemplarily illustrated in FIG. 3A, to maximize strength and elasticity of the mesh wire 112. The cross bar mesh has the elastic forces of wires in the cross bar mesh, and therefore is more elastic in a horizontal direction. A dentist can select a direction to position the cross bar mesh to expand or stabilize the arch form. The cross bar mesh is soldered to the arch wire 104 and/or to the primary frame wire 109 exemplarily illustrated in FIGS. 3B-3D.

FIG. 15B exemplarily illustrates an embodiment of the mesh wire 112 configured, for example, as an orthogonal mesh. The mesh wire 112 configured as an orthogonal mesh offers different directions of elastic force along the mesh configuration. The orthogonal mesh provides more rigidity than the cross bar mesh exemplarily illustrated in FIG. 15A. In an embodiment, the orthogonal mesh and the cross bar mesh are combined based on the desired movement needed in the arch form.

FIG. 15C exemplarily illustrates an embodiment of the mesh wire 112 configured, for example, as an orthogonal mesh. In this embodiment, the wires of the mesh are arranged at right angles to each other. In an embodiment, the mesh wire 112 is infused in the first soft enclosing layer 105 exemplarily illustrated in FIG. 3A. This embodiment of the mesh wire 112 helps in better adhesion of the first soft enclosing layer 105 exemplarily illustrated in FIG. 3A, to the tooth surface.

Figure 16:
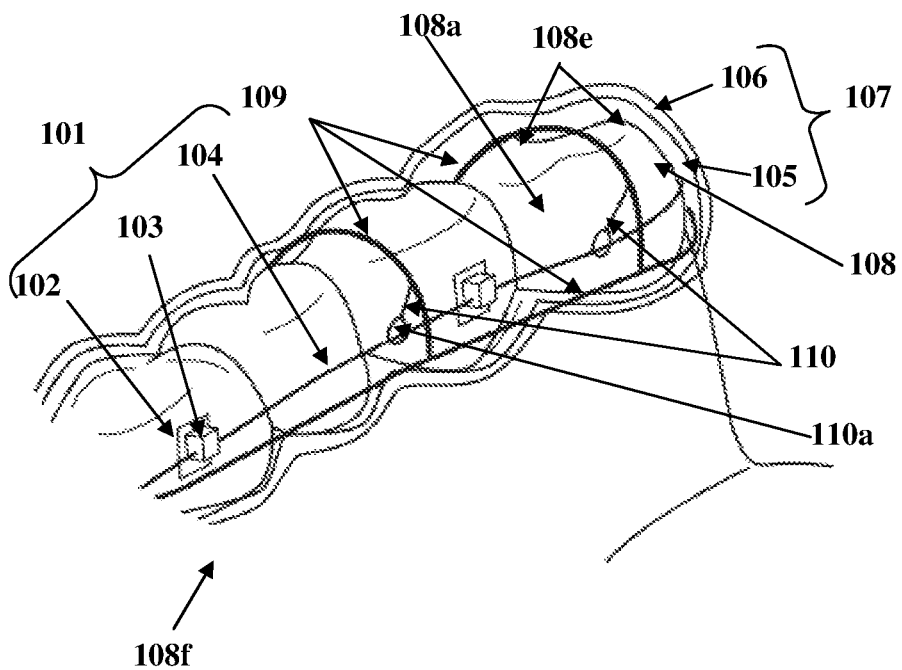
FIG. 16 exemplarily illustrates a partial perspective view of an embodiment of the detachable orthodontic bracket and wire system shown in FIG. 3A, showing an embodiment of the secondary frame wires through which the arch wire is passed.

FIG. 16 exemplarily illustrates a partial perspective view of an embodiment of the detachable orthodontic bracket and wire system 101 exemplarily illustrated in FIG. 3A, showing an embodiment of the secondary frame wires 113, for example, loop wires 110 through which the arch wire 104 is passed. In this embodiment, the arch wire 104 passes through the loop wire 110 that is secured to and extends from the primary frame wire 109 on the lingual surface 108a of the teeth 108. The loop wire 110 can be welded or soldered to the arch wire 104 and/or the primary frame wire 109 or hinged along the arch wire 104 which allows limited movement such as translation and rotation of targeted teeth 108 around the arch wire 104. Thus, the loop wire 110 is secured around each tooth, and each tooth can move along the arch wire 104 and respond to the orthodontic forces. In an embodiment, a circular loop 110a or a double circular loop of the loop wire 110 secures the arch wire 104 with the first soft enclosing layer 105. The arch wire 104 runs through the center of the circular loop 110a of the loop wire 110 to allow sliding movement of targeted teeth 108 along the arch wire 104.

Figure 17:
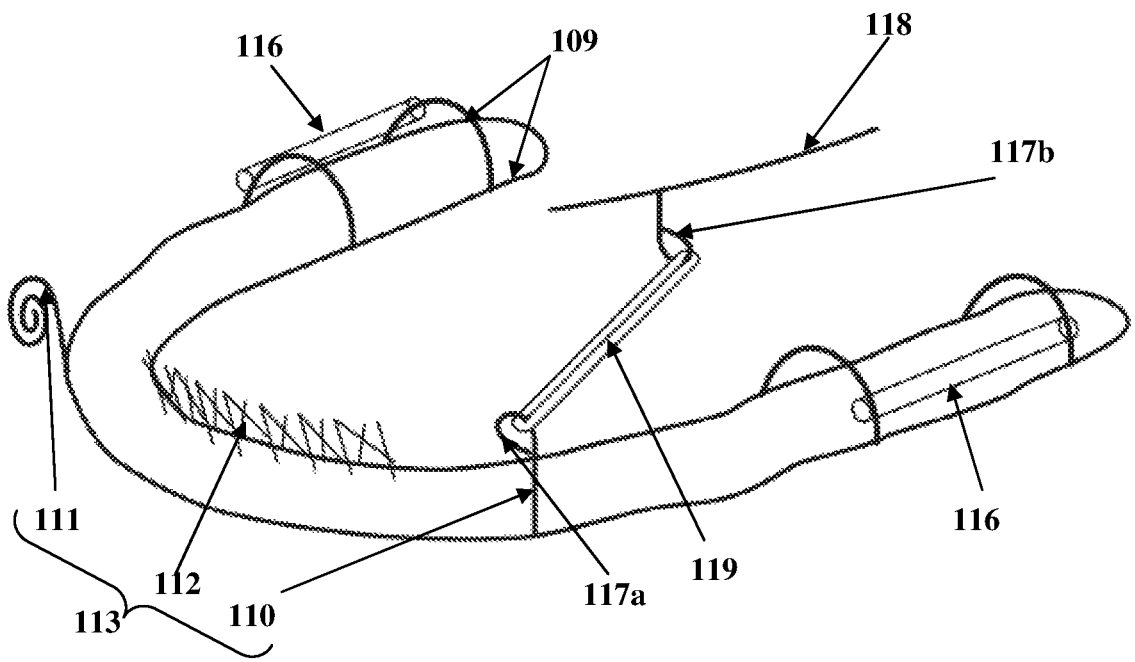
FIG. 17 exemplarily illustrates a perspective view of a primary frame wire of the embodiment of the detachable orthodontic bracket and wire system shown in FIG. 3A, showing positioning of tubes on the primary frame wire and elastics on the secondary frame wires.

FIG. 17 exemplarily illustrates a perspective view of a primary frame wire 109 of the embodiment of the detachable orthodontic bracket and wire system 101 shown in FIG. 3A, showing positioning of tubes 116 and elastics 119 on the secondary frame wire 113. In an embodiment, the detachable orthodontic bracket and wire system 101 further comprises tubes 116 fixedly attached to the primary frame wire 109 for engaging with an extraoral orthodontic appliance (not shown), for example, face gear, headgear exemplarily illustrated in FIG. 19, cervical headgear, high pull headgear, a reverse pull face mask, etc. The tubes 116 are soldered on to the primary frame wire 109 to engage the extraoral orthodontic appliance. In an embodiment, the detachable orthodontic bracket and wire system 101 is combined with an airway management appliance, for example, a mandibular advancing snore guard for patients who are aged and critically require airway management to preclude obstruction of the airway by the detachable orthodontic bracket and wire system 101 and their own airway structure.

In another embodiment, the detachable orthodontic bracket and wire system 101 further comprises one or more hooks 117a and 117b positioned on one or more canines and/or one or more molars of the lower jaw 108f or the upper jaw (not shown). In an embodiment, the hook 117a is a part of the loop wire 110. The hook 117b is connected to a wire 118 that extends from the upper jaw. The hooks 117a and 117b are added to the anchoring teeth 108 from the lower arch of the lower jaw 108f exemplarily illustrated in FIG. 1, FIG. 2, and FIGS. 3A-3B, and the upper arch of the upper jaw respectively as exemplarily illustrated in FIG. 17. In another embodiment, the detachable orthodontic bracket and wire system 101 further comprises one or more elastics 119 positioned on the hooks 117*a* and 117*b* as exemplarily illustrated in FIG. 17. The elastic 119 is hooked to the hook 117*a* of the loop wire 110 and to the hook 117*b* extending from the wire 118 connected to the upper jaw. The elastics 119 engage between the teeth 108 in the upper jaw or the lower jaw 108*f*. The elastics 119 connect the upper jaw and the lower jaw 108*f* to provide an optimal orthodontic force to correct conditions such as a cross bite, an over bite, etc. In an embodiment, the elastics 119 are engaged between the teeth 108 in the upper jaw and the lower jaw 108*f*, and the teeth 108 embraced by the secondary frame wires 113 can slide along the arch wire 104 to correct the cross bite and other dental malalignments.

In an embodiment, since the detachable orthodontic bracket and wire system 101 disclosed herein substantially increases the strength of the brackets 103 on the teeth 108, elastics 119, and springs (not shown) from a fixed arch wire and bracket system can be incorporated in the detachable orthodontic bracket and wire system 101. In another embodiment, since an occlusal force between teeth 108 of the upper jaw (not shown) and teeth 108 of the lower jaw 108*f* exemplarily illustrated in FIG. 1, FIG. 2, and FIGS. 3A-3B, are required for the movement of the teeth 108, for example, about 1 mm to about 3 mm diameter and about 0.5 mm to about 1.5 mm height cylinders or cone shaped discs (not shown) are configured on an occlusal surface (not shown) of the teeth 108 to provide an additional orthodontic force to move the teeth 108.

Figure 18:
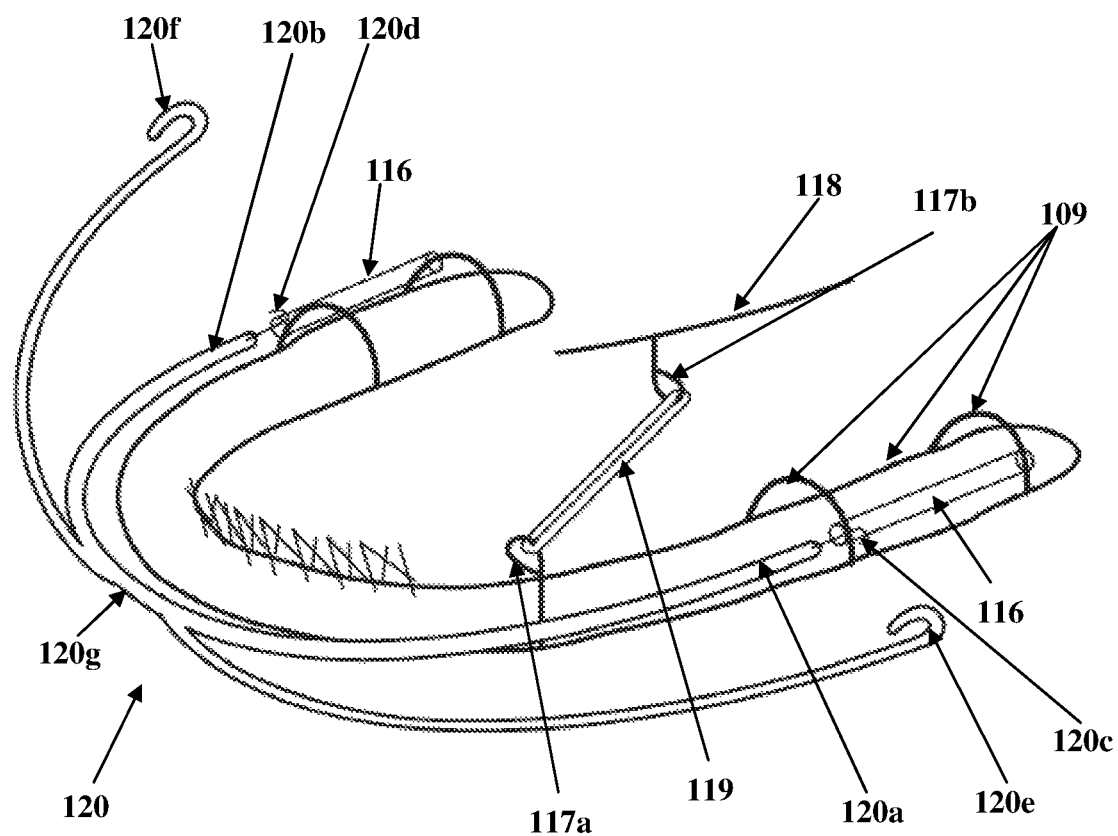
FIG. 18 exemplarily illustrates a perspective view of a primary frame wire of the embodiment of the detachable orthodontic bracket and wire system shown in FIG. 3A, showing positioning of a face bow for an extraoral orthodontic appliance attached to the tubes on the primary frame wire.
Figure 19:
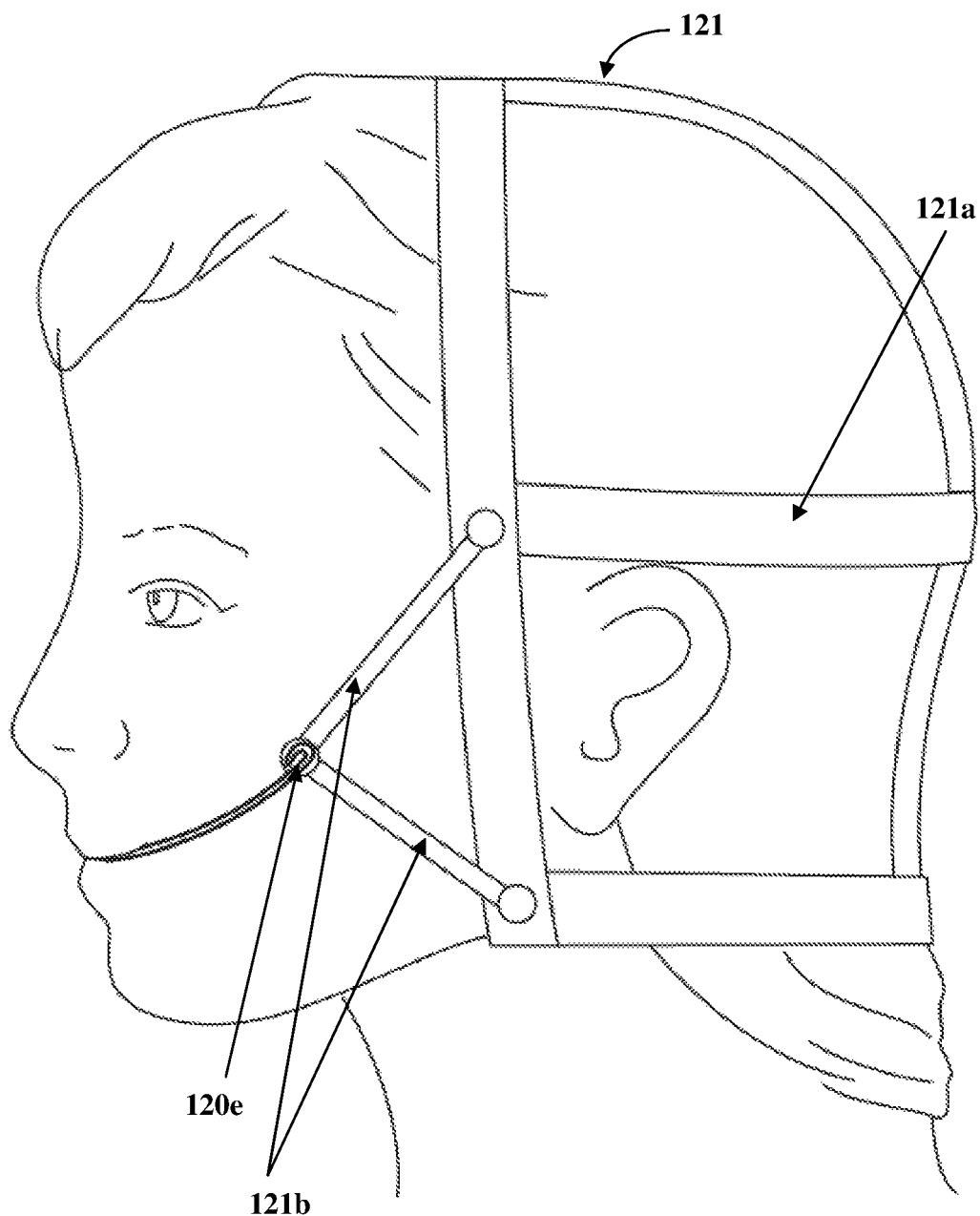
FIG. 19 exemplarily illustrates a right side elevation view of an extraoral orthodontic appliance worn by a patient and fixed to hooks of the face bow shown in FIG. 18.

FIG. 18 exemplarily illustrates a perspective view of a primary frame wire 109 of the embodiment of the detachable orthodontic bracket and wire system 101 shown in FIG. 3A, showing positioning of a face bow 120 for an extraoral orthodontic appliance, for example, for head gear 121 exemplarily illustrated in FIG. 19, attached to the tubes 116 on the primary frame wire 109. The face bow 120 comprises at least two arms 120*a* and 120*b* connected to the tubes 116 on the primary frame wire 109 via hooks 120*c* and 120*d* respectively. The face bow 120 further comprises hook elements 120*e* and 120*f* that extend from the center 120*g* of the facebow 120 and away from the two arms 120*a* and 120*b* of the face bow 120 as exemplarily illustrated in FIG. 18. The hook elements 120*e* and 120*f* of the face bow 120 allow attachment of the head gear 121 to a patient's head as exemplarily illustrated in FIG. 19.

FIG. 19 exemplarily illustrates a right side elevation view of an extraoral orthodontic appliance, for example, head gear 121 worn by a patient and fixed to the hook elements 120*e* and 120*f* of the face bow 120 shown in FIG. 18. The head gear 121 comprises a strap 121*a*, for example, made of fabric that fits around the patient's head or the back of the patient's neck. The primary frame wire 109 with the face bow 120 for the head gear 121 exemplarily illustrated in FIG. 18, is positioned on the patient's teeth 108 in the patient's mouth. The strap 121*a* of the head gear 121 is then connected to the hook elements 120*e* and 120*f* of the face bow 120 exemplarily illustrated in FIG. 19, via connecting straps 121*b*.

Figure 20A:
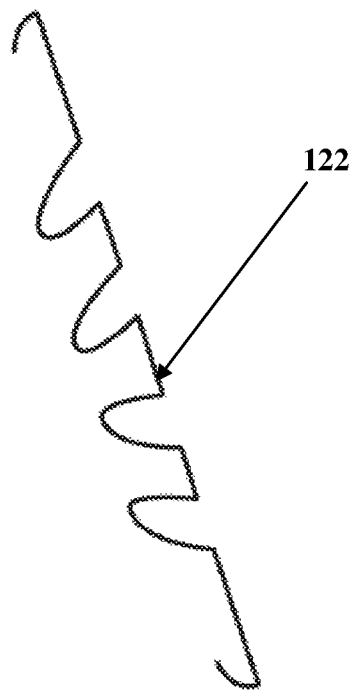
FIG. 20A exemplarily illustrates a pre-bended wire.
Figure 20B:
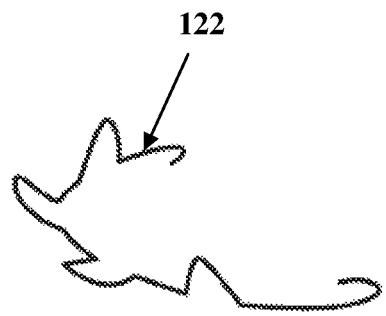
FIG. 20B exemplarily illustrates the pre-bended wire in an arch form.
Figure 20C:
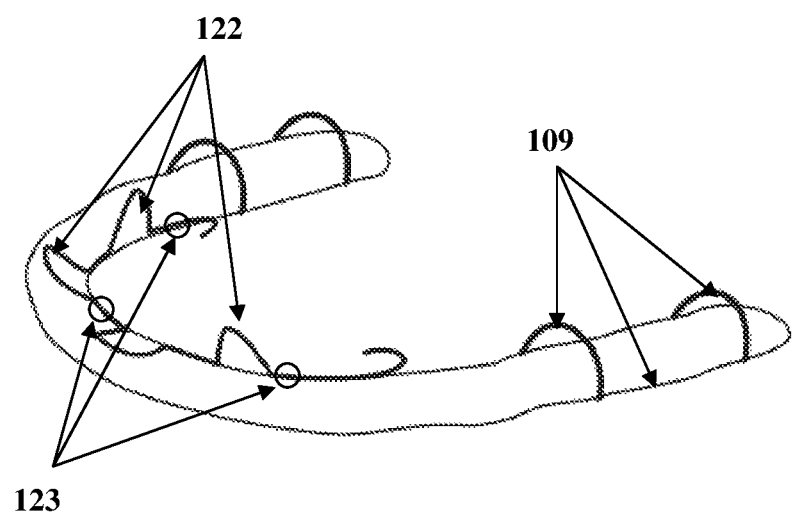
FIG. 20C exemplarily illustrates a perspective view of the primary frame wire with the pre-bended wire in the arch form shown in FIG. 20B added thereto, in an embodiment of the detachable orthodontic bracket and wire system.

FIGS. 20A-20B exemplarily illustrate a pre-bended wire 122. In an embodiment, a pre-bended wire 122 in an arch form exemplarily illustrated in FIG. 20B, is added to the primary frame wire 109 for strengthening the primary frame wire 109, providing elasticity to the primary frame wire 109, and allowing the primary frame wire 109 to sustain three-dimensional bending forces, rotational forces, and torque. In an embodiment (not shown), the pre-bended wire 122 in the arch form exemplarily illustrated in FIG. 20B, is added to the primary frame wire 109 and/or the secondary frame wires 113 exemplarily illustrated in FIG. 17, for strengthening the primary frame wire 109 and/or the secondary frame wires 113, providing elasticity to the primary frame wire 109 and/or the secondary frame wires 113, and allowing the primary frame wire 109 and/or the secondary frame wires 113 to sustain three-dimensional bending forces, rotational forces, and torque. The pre-bended wire 122 exemplarily illustrated in FIG. 20A, is bent in an arch form exemplarily illustrated in FIG. 20B, before mounting the pre-bended wire 122 on the primary frame wire 109. The pre-bended wire 122 are mounted on the primary frame wire 109 using mounting loops 123 as exemplarily illustrated in FIG. 20C. In an embodiment, the pre-bended wire 122 is used instead of the mesh wire 112 exemplarily illustrated in FIG. 17, when the teeth 108 are crowded and an extra expansion force is needed.

The pre-bended wires 122 provide more elasticity and three-dimensional bending, rotational and torque forces to the primary frame wire 109 and/or the secondary frame wires 113. Since the pre-bended wire 122 is bent in a three-dimensional space, a responding force of the pre-bended wire 122 can be transferred and exerted over a large range of the three-dimensional space and the elasticity of the primary frame wire 109 and the secondary frame wires 113 is also maintained which is necessary for orthodontic movement. Each pre-bended wire 122 offers a responding force at the end of each primary frame wire 109 and/or each of the secondary frame wires 113 in a particular direction. The pre-bended wires 122 are inserted into slot channels (not shown) soldered in the primary frame wire 109. In an embodiment, the pre-bended wires 122 are inserted into slot channels (not shown) soldered in each of the secondary frame wires 113.

The primary frame wire 109 and/or the secondary frame wires 113 maintain the basic shape and elasticity of the enclosing layer 107, for a long duration of time. The arch wire 104 exemplarily illustrated in FIG. 3A-3D, forms an optimal arch form and provides a correcting orthodontic force to the teeth 108 to move to a new position. The secondary frame wires 113 including the mesh element 115 exemplarily illustrated in FIG. 14, and the pre-bended wires 122 provide additional anchorage force to each individual tooth, while allowing relative tooth movement to reposition the teeth 108 precisely along the arch wire 104. The orthodontic forces are stabilized from the primary frame wire 109 and precision engineered by the arch wire 104, and distributed precisely and optimally to each individual tooth. The final forces are precisely anchored onto those teeth 108 that are bonded to the detachable orthodontic bracket and wire system 101.

Since the detachable orthodontic bracket and wire system 101 is removable, the detachable orthodontic bracket and wire system 101 can be used in conventional removable orthodontic appliances, for example, a Nance or Pendex appliance, a transpalatal arch, a holding arch, a space maintainer, a twin appliance, a Hawley appliance, a space expander, a quad helix, a pendulum appliance, etc., with enhanced esthetic appeal from a facial view as a metal wire at the facial side of the arch is no longer needed. The detachable orthodontic bracket and wire system 101 can also be used in an intraoral functional appliance such as a lip bumper and palatal supporting appliance by adding a layer of a plastic shield (not shown) to preclude a lip or palate from pushing the teeth 108. The layer of plastic shield provides additional anchoring beside the gum and alveolar ridge.

Figure 21:
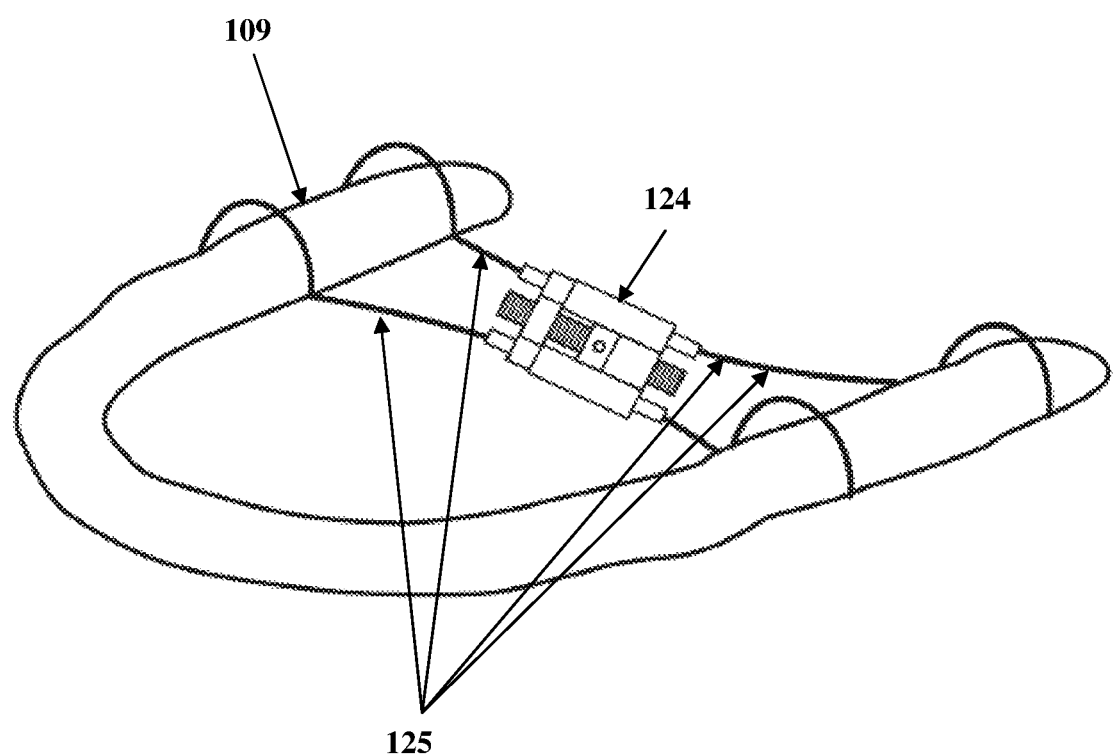
FIG. 21 exemplarily illustrates a perspective view of the primary frame wire attached to a palatal expander.
Figure 22:
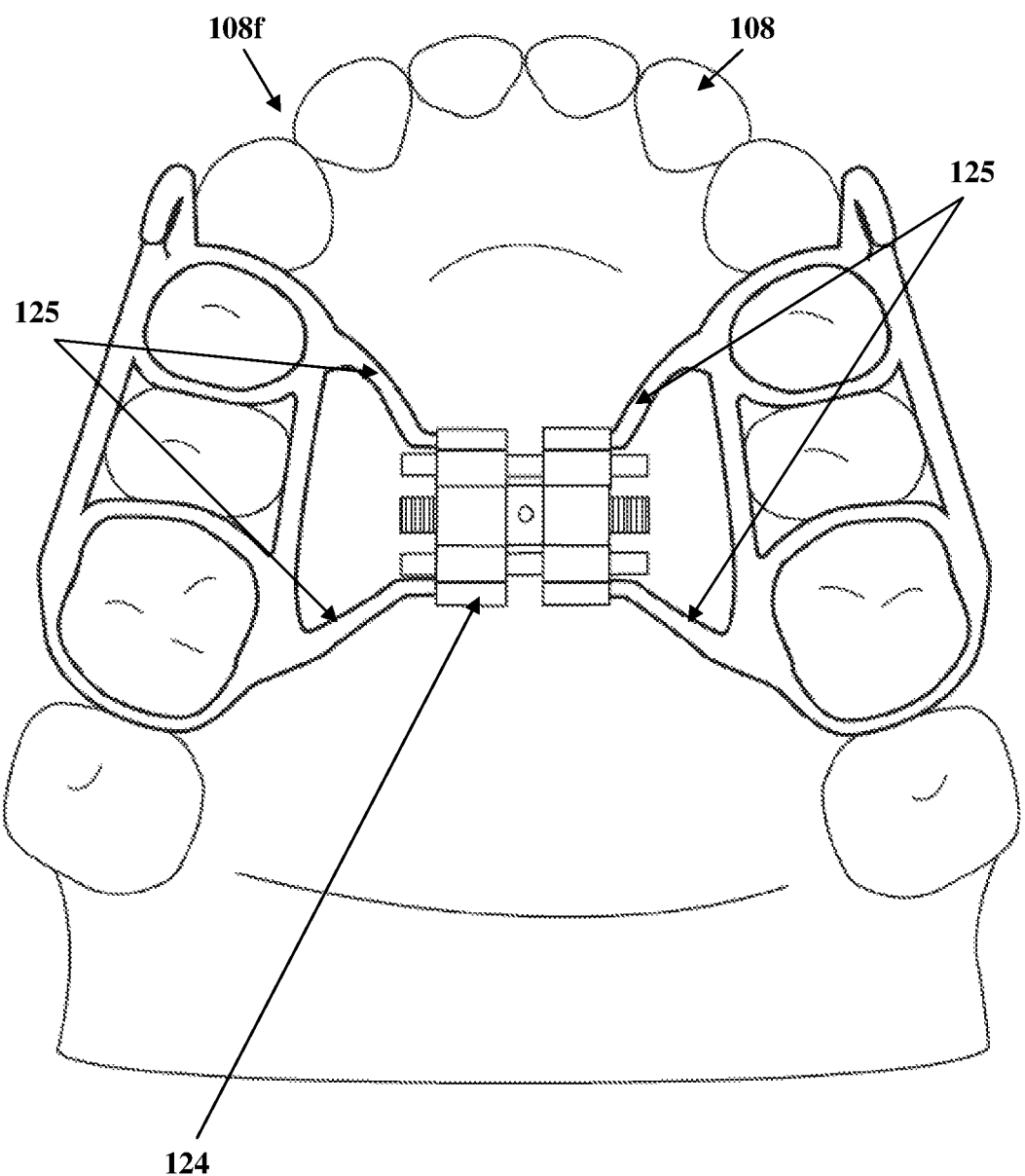
FIG. 22 exemplarily illustrates a top plan view of the primary frame wire attached to the palatal expander.

FIGS. 21-22 exemplarily illustrate a perspective view and a top plan view of the primary frame wire 109 attached to a palatal expander 124 respectively. In an embodiment, a palatal expander 124 is connected to the primary frame wire 109 for providing a strong and controlled expansion force to expand the dental arch (not shown). The palatal expander 124 is used when the dental arch needs further expansion. The palatal expander 124 provides a strong and controlled force to expand the dental arch. The palatal expander 124 is fixed to the primary frame wire 109 through legs 125 that are welded or soldered to the primary frame wire 109.

Figure 23A:
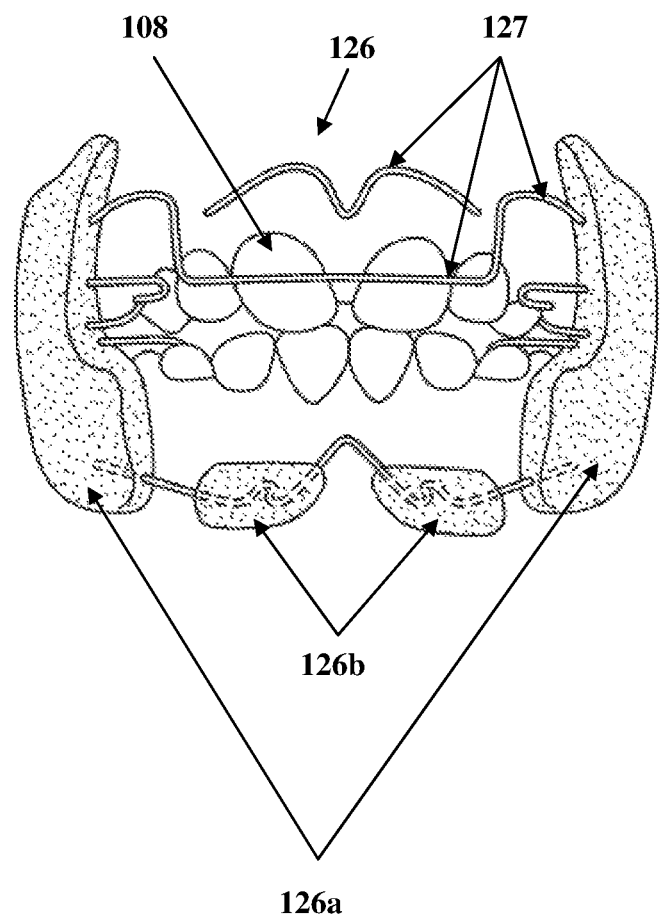
FIGS. 23A-23C exemplarily illustrate embodiments showing frame wires used for connecting a Frankel appliance to teeth.
Figure 23B:
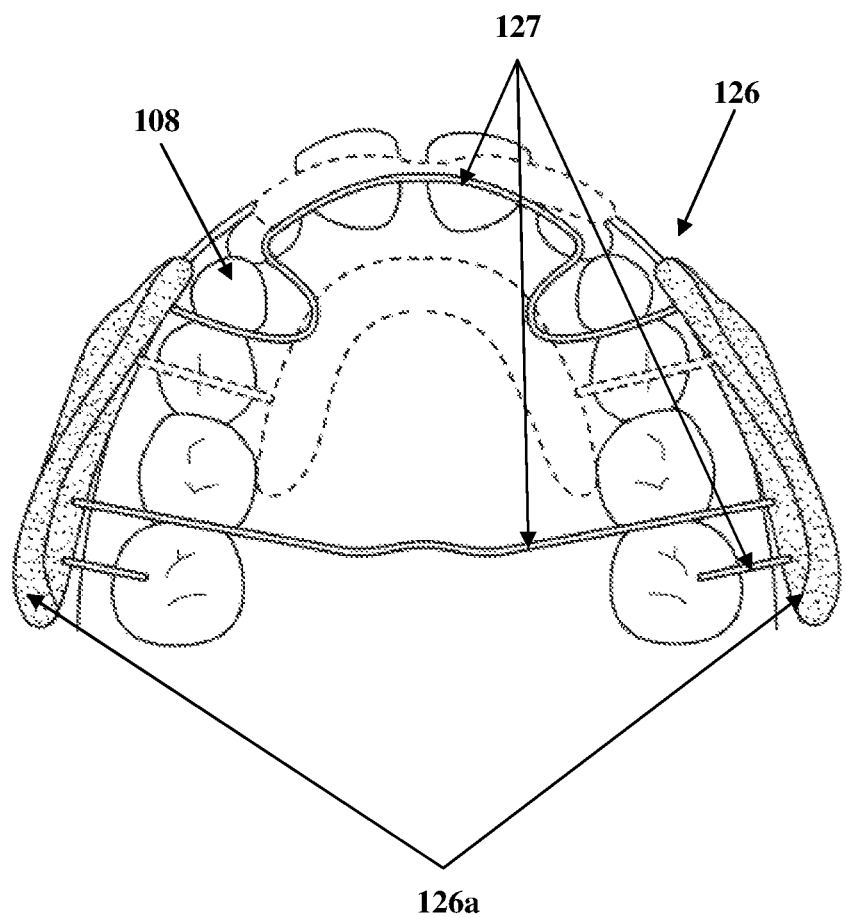
Figure 23C:
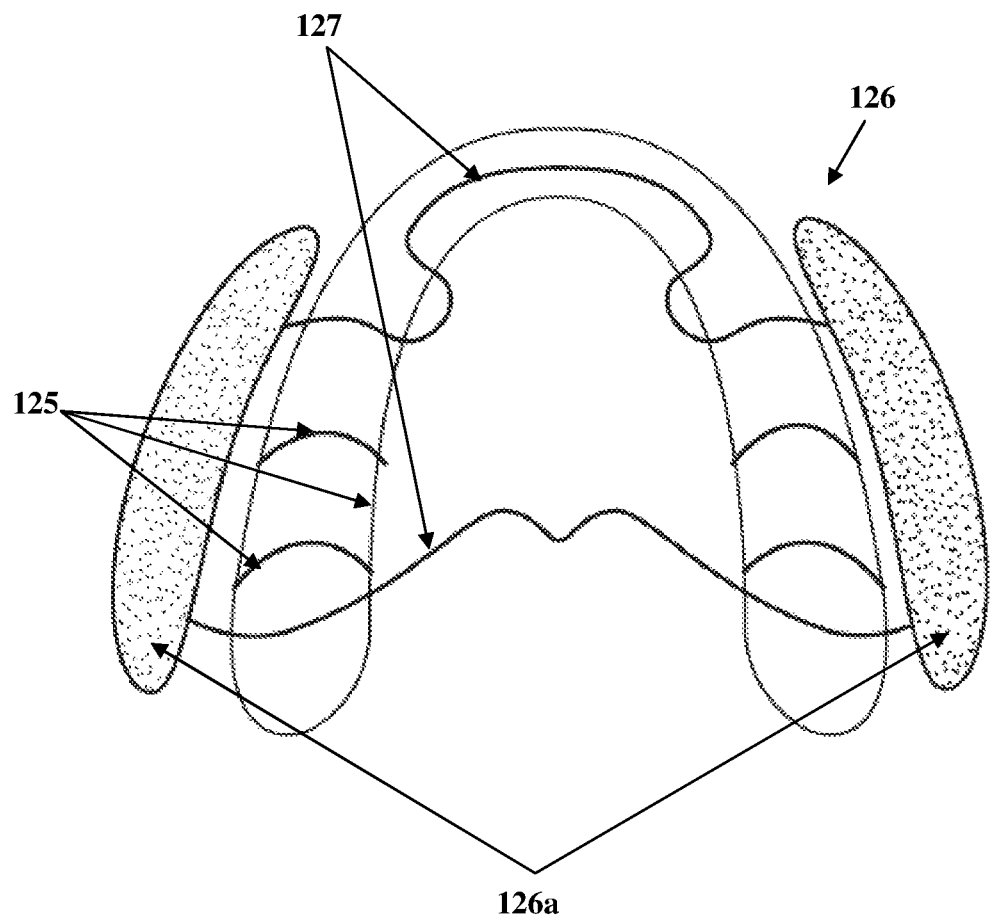

FIGS. 23A-23C exemplarily illustrate embodiments showing frame wires 127 used for connecting a Frankel appliance 126 to teeth 108. The Frankel appliance 126 is used in the treatment of functional disorders associated with dento skeletal malformation. The Frankel appliance 126 modifies the growth of the teeth 108 and jaws (not shown), while eliminating the functional disorders during normal development of the teeth 108. In addition to the functional disorders associated with the development of teeth 108, the Frankel appliance 126 is also used in the treatment of malocclusions, that is, an improper alignment of the teeth 108 when the jaws are closed. The Frankel appliance 126 comprises buccal shields 126a and buccal pads 126b. The buccal shields 126a and the buccal pads 126b of the Frankel appliance 126 are connected to the teeth 108 through the frame wires 127. The frame wires 127 are soldered or welded to the primary frame wire 109 exemplarily illustrated in FIG. 17.

Figure 24:
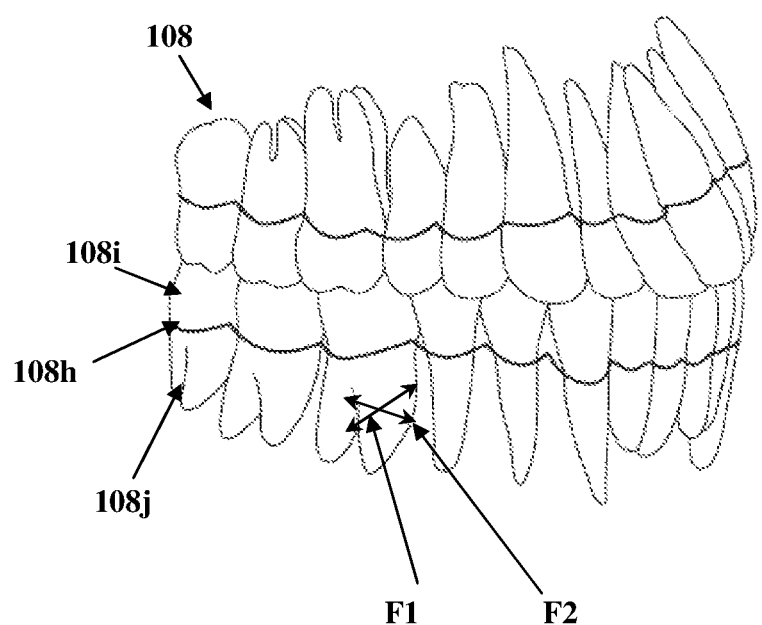
FIG. 24 exemplarily illustrates forces and torque applied on roots of teeth by the detachable orthodontic bracket and wire system.

FIG. 24 exemplarily illustrates forces and torque applied on roots 108j of teeth 108 by the detachable orthodontic bracket and wire system 101 exemplarily illustrated in FIGS. 3A-3D. The detachable orthodontic bracket and wire system 101 exemplarily illustrated in FIGS. 3A-3D, is configured using software that models movement of the teeth 108 with root formation comprising length of roots 108j and three-dimensional orientation of the roots 108j. The root 108j of the teeth 108 is separated from crown 108i by a gum line interface 108h. The torque acting on the root 108j results in a torque motion that is exemplarily illustrated by F1 in FIG. 24. The torque motion F1 acts in a lingual and a facial direction as exemplarily illustrated by F1 and moves the roots 108j of teeth 108 in the lingual and the facial direction. The force exerted on the root 108j results in a tipping motion F2 that acts in mesial and distal direction of the roots 108j. Due to the motion F2, the teeth 108 are moved in the mesial and distal direction in addition to the lingual and facial direction. The combined effect of the torqueing motion F1 and motion generated by the force F2 results in the proper alignment of the teeth 108. Since the detachable orthodontic bracket and wire system 101 provides a precise long lasting force to move the teeth 108, the software that models the movement of the teeth 108 considers the root formation comprising the length of the roots 108j and the three-dimensional orientation of the roots 108j to accurately predict the amount and direction of force needed to move the teeth 108.

The foregoing examples have been provided merely for the purpose of explanation and are in no way to be construed as limiting of the removable orthodontic appliance 100 comprising the detachable orthodontic bracket and wire system 101 disclosed herein. While the removable orthodontic appliance 100 comprising the detachable orthodontic bracket and wire system 101 has been described with reference to various embodiments, it is understood that the words, which have been used herein, are words of description and illustration, rather than words of limitation. Furthermore, although the removable orthodontic appliance 100 comprising the detachable orthodontic bracket and wire system 101 has been described herein with reference to particular means, materials, and embodiments, the removable orthodontic appliance 100 comprising the detachable orthodontic bracket and wire system 101 is not intended to be limited to the particulars disclosed herein; rather, the removable orthodontic appliance 100 comprising the detachable orthodontic bracket and wire system 101 extends to all functionally equivalent structures, methods and uses, such as are within the scope of the appended claims. Those skilled in the art, having the benefit of the teachings of this specification, may effect numerous modifications thereto and changes may be made without departing from the scope and spirit of the removable orthodontic appliance 100 comprising the detachable orthodontic bracket and wire system 101 disclosed herein in its aspects.

We claim:

1. An orthodontic bracket and wire system detachably attachable to teeth for guiding alignment of teeth of one of an upper jaw and a lower jaw of a patient, said orthodontic bracket and wire system comprising:
   a plurality of bracket bases configured to be positioned on one or more of a lingual surface and a facial surface of said teeth, each of said bracket bases comprising:
      a first surface configured to attach rigidly to each of said one or more of said lingual surface and said facial surface of said teeth;
      a second surface configured to oppose said each of one or more of said lingual surface and said facial surface of said teeth; and
      at least one first interlocking element configured to detachably attach to said second surface of said each of said bracket bases and positioned in one of a direction substantially perpendicular to and a direction substantially parallel to said second surface of said each of said bracket bases;
   a plurality of brackets, each of said brackets comprising at least one second interlocking element configured to interlock with said at least one first interlocking element of said each of said bracket bases in said one of said direction substantially perpendicular to and said direction substantially parallel to said second surface of said each of said bracket bases, said each of said brackets further comprising a slot channel passing through said each of said brackets;
   at least one arch wire configured to be inserted through said slot channel of said each of said brackets on said one or more of said lingual surface and said facial surface of said teeth and extending from a molar region on a first side to a molar region on a second side of a dental arch;
   a primary frame wire configured to be positioned on said facial surface and said lingual surface of said teeth and traversing from said facial surface to said lingual surface of said teeth through cusps of said teeth, said primary frame wire configured to secure and anchor said brackets interlocked to said bracket bases to said teeth and provide strong orthodontic forces to said teeth;
   one or more secondary frame wires configured to anchor to one of said at least one arch wire and said primary frame wire and configured to be rigidly positioned around each of said teeth individually to allow said each of said teeth to move independent of each other;

said at least one arch wire, said brackets, said primary frame wire and said one or more secondary frame wires coated with a hard plastic material; and said at least one arch wire, said brackets, said primary frame wire and said one or more secondary frame wires infused and rigidly anchored within one or more of an inner lingual side and an inner facial side of enclosing layers, said enclosing layers extending from said lingual surface to said facial surface of said teeth, and wherein said enclosing layers comprise:
a soft enclosing layer extending from said lingual surface to said facial surface of said teeth, wherein said soft enclosing layer is elastic; and
a hard enclosing layer enclosing said soft enclosing layer and extending from said lingual surface to said facial surface of said teeth, wherein said hard enclosing layer is rigid.

2. The orthodontic bracket and wire system of claim 1, wherein said slot channel is configured with a predefined cross section to accommodate said arch wire configured with said predefined cross section, wherein said predefined cross section is one of a rectangular cross section and a circular cross section.

3. The orthodontic bracket and wire system of claim 1, wherein said one or more secondary frame wires are configured in one or more of a loop configuration, a spiral configuration, a cross bar mesh configuration and an orthogonal mesh configuration.

4. The orthodontic bracket and wire system of claim 1, further comprising a cross bar positioned below each of said at least one first interlocking element of said each of said bracket bases, wherein said each of said brackets further comprises a receptacle to engage said cross bar and restrict movement of said each of said brackets over said each of said bracket bases.

5. The orthodontic bracket and wire system of claim 1, wherein said at least one first interlocking element of said each of said bracket bases comprises one of a ball projection and a socket, and wherein said at least one second interlocking element of said each of said brackets comprises a corresponding one of said socket and said ball projection to allow interlocking of said at least one first interlocking element to said at least one second interlocking element.

6. A detachable orthodontic bracket and wire system for guiding alignment of teeth of one of an upper jaw and a lower jaw of a patient, said orthodontic bracket and wire system comprising:
a plurality of bracket bases configured to be positioned on one or more of a lingual surface and a facial surface of said teeth, each of said bracket bases comprising:
a first surface configured to rigidly attach to each of said one or more of said lingual surface and said facial surface of said teeth;
a second surface configured to oppose said each of one or more of said lingual surface and said facial surface of said teeth; and
at least one first interlocking element configured to attach to said second surface of said each of said bracket bases and positioned in one of a direction substantially perpendicular to and a direction substantially parallel to said second surface of said each of said bracket bases;
a plurality of brackets, each of said brackets comprising a slot channel passing through said each of said brackets, said each of said brackets further comprising at least one second interlocking element configured to interlock with said at least one first interlocking element of said each of said bracket bases in said one of said direction substantially perpendicular to and said direction substantially parallel to said second surface of said each of said bracket bases, wherein said at least one first interlocking element of said each of said bracket bases comprises one of a ball projection and a socket, wherein said at least one second interlocking element of said each of said brackets comprises a corresponding one of said socket and said ball projection to allow interlocking of said at least one first interlocking element to said at least one second interlocking element;
a cross bar positioned below each of said at least one first interlocking element of said each of said bracket bases, wherein said each of said brackets further comprises a receptacle to engage said cross bar and restrict movement of said each of said brackets over said each of said bracket bases, wherein said crossbar and said interlocking by said ball projection and said socket enables rotational force to be applied to said tooth;
at least one arch wire configured to be inserted through said slot channel of said each of said brackets on said one or more of said lingual surface and said facial surface of said teeth and extending from a molar region on a first side to a molar region on a second side of a dental arch;
a primary frame wire configured to be positioned on said facial surface and said lingual surface of said teeth and traversing from said facial surface to said lingual surface of said teeth through cusps of said teeth, said primary frame wire configured to secure and anchor said brackets interlocked to said bracket bases to said teeth and provide orthodontic forces to said teeth;
one or more secondary frame wires configured to anchor to one of said at least one arch wire and said primary frame wire and configured to rigidly position around each of said teeth individually to allow said each of said teeth to move independent of each other;
said at least one arch wire, said brackets, said primary frame wire and said one or more secondary frame wires coated with a hard plastic material;
said at least one arch wire, said brackets, said primary frame wire and said one or more secondary frame wires infused and rigidly anchored within one or more of an inner lingual side and an inner facial side of enclosing layers, said enclosing layers extending from said lingual surface to said facial surface of said teeth, wherein said enclosing layers comprise a soft enclosing layer and a hard enclosing layer;
said soft enclosing layer extending from said lingual surface to said facial surface of said teeth, wherein said soft enclosing layer is elastic;
said hard enclosing layer enclosing said soft enclosing layer and extending from said lingual surface to said facial surface of said teeth, wherein said hard enclosing layer is rigid; and
hooks attached at an extremity of said secondary frame wires, wherein an elastic band is fixed between said hooks, wherein said elastic band connects said upper jaw and said lower jaw, and wherein said elastic band provides an orthodontic force to correct conditions comprising a cross bite and an over bite.

* * * * *